United States Patent
Olsen et al.

(10) Patent No.: US 9,901,284 B2
(45) Date of Patent: Feb. 27, 2018

(54) COORDINATION OF FUNCTIONAL MRI SCANNING AND ELECTRICAL STIMULATION THERAPY

(75) Inventors: James M. Olsen, Plymouth, MN (US); Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 1721 days.

(21) Appl. No.: 13/087,736

(22) Filed: Apr. 15, 2011

(65) Prior Publication Data

US 2011/0257509 A1  Oct. 20, 2011

Related U.S. Application Data

(60) Provisional application No. 61/325,185, filed on Apr. 16, 2010.

(51) Int. Cl.
| | |
|---|---|
| *A61B 5/055* | (2006.01) |
| *A61N 1/372* | (2006.01) |
| *A61B 5/00* | (2006.01) |
| *A61N 1/362* | (2006.01) |

(52) U.S. Cl.
CPC .......... *A61B 5/055* (2013.01); *A61B 5/7203* (2013.01); *A61N 1/37235* (2013.01); *A61N 1/362* (2013.01); *A61N 1/37247* (2013.01)

(58) Field of Classification Search
CPC ...... A61B 5/055; A61B 5/7203; A61N 1/362; A61N 1/37235; A61N 1/37247
See application file for complete search history.

(56) References Cited

U.S. PATENT DOCUMENTS

| | | | |
|---|---|---|---|
| 5,733,247 A * | 3/1998 | Fallon | 600/410 |
| 2002/0133071 A1* | 9/2002 | Wolff et al. | 600/422 |
| 2005/0070787 A1 | 3/2005 | Zeijlemaker | |
| 2008/0027306 A1* | 1/2008 | Washburn et al. | 600/410 |
| 2009/0138058 A1* | 5/2009 | Cooke et al. | 607/5 |
| 2009/0234218 A1* | 9/2009 | Washburn et al. | 600/410 |
| 2009/0281595 A1* | 11/2009 | King et al. | 607/46 |

* cited by examiner

*Primary Examiner* — Ruth S Smith
(74) *Attorney, Agent, or Firm* — Shumaker & Sieffert, P.A.

(57) ABSTRACT

Changes in electrical stimulation therapy delivered via a medical device are coordinated with Functional Magnetic Resonance Imaging (fMRI) scans. In one example, a medical device delivers electrical stimulation therapy to a patient in an MRI unit, where the medical device is configured to cycle electrical stimulation therapy between a plurality of stimulation states. An indication that the medical device will cycle the electrical stimulation therapy or has cycled the electrical stimulation therapy while the patient is in the MRI unit or being imaged by the MRI unit is generated, and an MRI scan of the patient via an MRI workstation is initiated based on the indication. In another example, a medical device detects activation of an MRI scan and automatically switches stimulation states based upon the detection of the MRI scan, such that the scan is associated with a particular stimulation state.

36 Claims, 9 Drawing Sheets

COORDINATION OF FUNCTIONAL MRI SCANNING AND ELECTRICAL STIMULATION THERAPY

This application claims the benefit of U.S. Provisional Application No. 61/325,185, entitled, "TECHNIQUES FOR SYNCHRONIZING FUNCTIONAL MRI SCANNING AND NEUROSTIMULATION THERAPY," and filed on Apr. 16, 2010, the entire content of which is incorporated herein by reference.

TECHNICAL FIELD

The disclosure relates to medical devices and, more particularly, to implantable medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include, for example, stimulation of nerve, muscle, or brain tissue, or other tissue within a patient. In some cases, an electrical stimulation system may be fully implanted within the patient. For example, an electrical stimulation system may include an implantable electrical stimulation generator and one or more implantable leads carrying electrodes. As another example, the electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

A clinician can select values for a number of programmable stimulation parameters in order to define the electrical stimulation therapy to be delivered to a patient. For example, the clinician may select a current or voltage amplitude of the stimulation, and various characteristics of the stimulation waveform. In addition, the clinician may specify an electrode configuration used to deliver stimulation, including selected electrode combinations and electrode polarities. If the stimulation is delivered in the form of pulses, for example, the clinician may specify a pulse amplitude, pulse width and pulse rate. A set of parameter values may be referred to as a stimulation program. A program group may include multiple programs. Multiple programs in a program group may be delivered on a simultaneous, time-interleaved, or overlapping basis.

SUMMARY

In general, the disclosure describes devices, systems, and techniques for coordinating changes in electrical stimulation therapy delivered via a medical device with Functional Magnetic Resonance Imaging (fMRI) scans. Functional MRI is a technique that can be used to identify areas of neural activity in response to a stimulus. The technique is performed in an MRI unit, and observes blood-oxygen-level dependence (BOLD) as a proxy for neural activity. Due to a low signal-to-noise ratio, several measurements under the same conditions are made in order to average out the noise component of the signal. As a result, fMRI may require the patient to be scanned several times with and without a stimulus. Coordinating changes to electrical stimulation therapy programs with fMRI scans may allow clinicians to correlate the stimulation therapy delivered with an fMRI scan.

In one example, the disclosure is directed to a method comprising, while a patient is in an MRI unit, generating an indication that a medical device that is configured to cycle electrical stimulation therapy between a plurality of stimulation states will cycle electrical stimulation therapy or has cycled electrical stimulation therapy, and initiating an MRI scan of the patient via an MRI workstation based on the indication.

In another example, the disclosure is directed to a system comprising an a MRI workstation configured to control a MRI unit that is configured to generate an MRI scan of a patient, a medical device configured to deliver electrical stimulation therapy to the patient while the patient is in the MRI unit or being imaged by the MRI unit, wherein the medical device is configured to cycle electrical stimulation therapy between a plurality of stimulation states, and a processor configured to generate an indication that the medical device will cycle the electrical stimulation therapy or has cycled the electrical stimulation therapy while the patient is in the MRI unit or being imaged by the MRI unit. The MRI workstation is configured to control the MRI unit to initiate the MRI scan of the patient based upon the indication.

In another example, the disclosure is directed to a system comprising means for delivering electrical stimulation therapy to a patient in an MRI unit according to a first program of a plurality of programs stored in a medical device, wherein the means for delivering electrical stimulation therapy is configured to cycle electrical stimulation therapy between a plurality of stimulation states, the first program being associated with a first stimulation state of the plurality of stimulation states. The system further comprises means for generating an indication that the medical device will cycle the electrical stimulation therapy or has cycled the electrical stimulation therapy while the patient is in the MRI unit or being imaged by the MRI unit and means for initiating an MRI scan of the patient via an MRI workstation based on the indication.

In another example, the disclosure is directed to a method comprising detecting an activation of a first MRI scan by an MRI unit, and after detecting activation of the first MRI scan, delivering, with a medical device, electrical stimulation therapy to a patient in the MRI unit or being imaged by the MRI unit, wherein the medical device is configured to provide electrical stimulation therapy in plurality of different stimulation states. The method further comprises subsequently detecting an activation of a second MRI scan by the MRI unit and changing a stimulation state of the medical device based on the detection of activation of the second MRI scan.

In another example, the disclosure is directed to a system comprising an MRI unit configured to generate an MRI scan of a patient, a medical device configured to deliver electrical stimulation therapy to the patient while the patient is in the MRI unit or being imaged by the MRI unit, wherein the medical device is configured to provide a plurality of different stimulation states, and a processor configured to detect activation of a first MRI scan by the MRI unit and control the medical device to deliver electrical stimulation therapy to the patient in the MRI unit or being imaged by the MRI unit after detecting the activation of the first MRI scan. The processor is further configured to subsequently detect an activation of a second MRI scan by an MRI unit and control the medical device to change a stimulation state based on the detection of activation of the second MRI scan.

In another example, the disclosure is directed to a system comprising means for detecting an activation of a first MRI scan by an MRI unit, means for delivering electrical stimulation therapy to a patient in the MRI unit or being imaged by the MRI unit after detecting activation of the first MRI scan, wherein the means for delivering electrical stimulation therapy is configured to provide a plurality of different stimulation states, means for detecting an activation of a second MRI scan by the MRI unit, and means for changing a stimulation state of the medical device based on the detection of activation of the second MRI scan.

In another example, the disclosure is directed to a method comprising receiving an indication that a medical device delivering electrical stimulation therapy to a patient in an MRI unit has switched from a first stimulation state to a second a stimulation state, wherein the medical device switches stimulation states without intervention from a user, while the medical device is in the second stimulation state, generating an MRI scan of the patient via an MRI unit based on the indication, and associating the second stimulation state with the MRI scan.

In another example, the disclosure is directed to a system comprising an MRI unit configured to generate an MRI scan of a patient, a medical device configured to deliver electrical stimulation therapy to the patient while the patient is in the MRI unit or being imaged by the MRI unit, wherein the medical device is configured to switch between a plurality of different stimulation states without intervention from a user, and a processor configured to receive an indication that the medical device has switched from a first stimulation state to a second a stimulation state, and, while the medical device is in the second stimulation state, control the MRI unit to generate an MRI scan of the patient via an MRI unit based on the indication and associate the second stimulation state with the MRI scan.

In another example, the disclosure is directed to a system comprising means for receiving an indication that a medical device delivering electrical stimulation therapy to a patient in an MRI unit has switched from a first stimulation state to a second a stimulation state, wherein the medical device switches stimulation states without intervention from a user, means for generating an MRI scan of the patient via an MRI unit based on the indication while the medical device is in the second stimulation state, and means for associating the second stimulation state with the MRI scan.

In another aspect, the disclosure is directed to an article of manufacture comprising a computer-readable storage medium. The computer-readable storage medium comprises computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. The computer-readable medium may be nontransitory.

The details of one or more aspects of the disclosure are set forth in the accompanying drawings and the description below. Other features, objects, and advantages will be apparent from the description and drawings, and from the claims.

DETAILED DESCRIPTION

This disclosure describes systems and techniques for coordinating changes in electrical stimulation therapy delivered via a medical device and fMRI scans. In order to determine the effect of electrical stimulation therapy on a patient, the patient may be scanned using fMRI techniques. The patient may be scanned while the electrical stimulation therapy is being cycled between different stimulation states, e.g., alternating between delivering stimulation therapy according to a first program and not delivering therapy, alternating between delivering stimulation therapy according to a first program and delivering stimulation therapy according to a second program, delivering stimulation according to each of a plurality of therapy programs in a linear (e.g., without any repeats) or repeating manner, and the like. Due to restrictions on what may be in the MRI scanning room during scanning, changes to the patient's therapy programming (e.g., selecting the therapy that occurs during the therapy cycling) may be made between scans or the medical device can be programmed such that therapy is cycled periodically according to a predictable and known schedule. Because changing the therapy programming between scans may be burdensome and time consuming, patients and clinicians may prefer that the medical device be programmed such that therapy is cycled periodically according to a schedule. However, in order to correlate each stimulation state (e.g., off, first program, second program, etc.) with an fMRI scan, it may be necessary to coordinate changes to electrical stimulation therapy programs with fMRI scans. Using various systems and techniques of this disclosure, changes to electrical stimulation therapy programs may be coordinated with fMRI scans.

Figure 1:
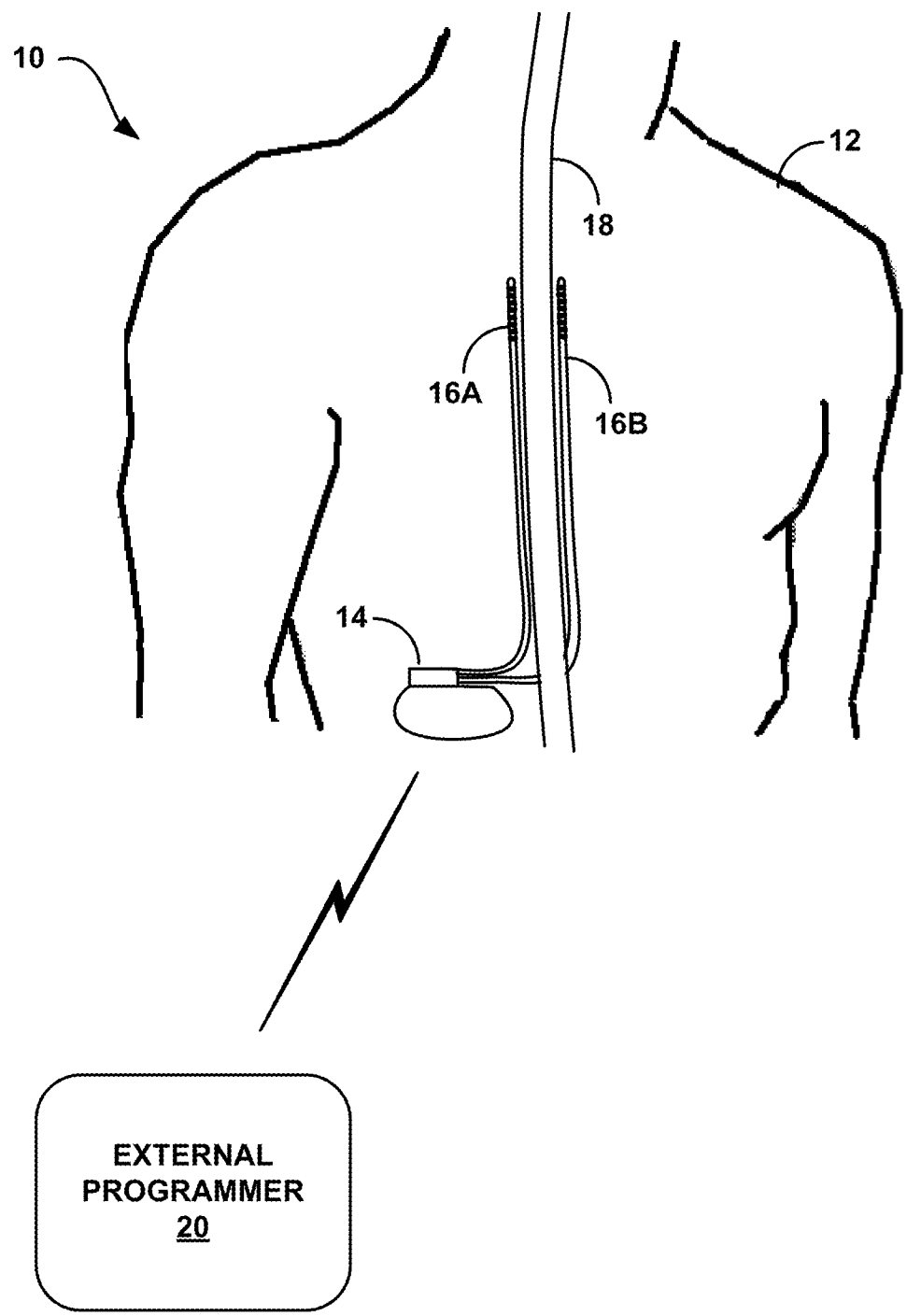
FIG. 1 is a schematic diagram illustrating a system including an implantable electrical stimulation system.

FIG. 1 is a schematic diagram illustrating an example implantable electrical stimulation system 10. FIG. 1 illustrates an example patient 12 and an implantable medical device (IMD) 14 implanted in the body of patient 12. While patient 12 is depicted as a human being in FIG. 1, patient 12 is not necessarily a human being. For example, patient 12 may be another animal. IMD 14 forms one part of a medical device system 10, which also includes an external programmer 20. As shown in FIG. 1, system 10 further includes a pair of stimulation leads 16A, 16B (collectively referred to as "leads 16") implanted within a patient 12 and coupled to IMD 14. Stimulation leads 16A, 16B may carry one or more electrodes through which IMD 14 can deliver electrical stimulation to a target tissue site within patient 12.

External programmer 20 may be a patient programmer or a clinician programmer, for example. A patient programmer may permit patient 12 to select particular electrical stimulation therapy programs specifying parameters for delivery of electrical stimulation, such as electrical stimulation voltage or current amplitude, pulse width, pulse rate, electrode configuration, duty cycle, or the like. The patient programmer may permit patient 12 to select individual programs, or groups of programs, or possibly adjust some of the parameters associated with the programs.

The patient programmer may be configured to permit patient 12 to control or adjust only a limited subset of the therapy parameters, rather than all of such therapy parameters, e.g., for safety reasons or simplicity in patient programmer operation. For example, the patient programmer may be configured to permit patient amplitude, pulse width, or pulse rate adjustments to be made only within a limited range, or to permit only particular sets of electrode configurations to be selected by patient 12. In contrast, a clinician programmer may be configured for use by a clinician or other caregiver, and permit a clinician to control or adjust a larger, and perhaps complete, set of therapy parameters, relative to the limited set of parameters adjustable via the patient programmer.

In some examples, IMD 14 may comprise an MRI safe or an MRI conditionally safe device. IMD 14 includes software and/or hardware features that result in IMD 14 being compatible with substantially all known MRI modalities and MRI scan parameters. However, an MRI conditionally safe device may include software and/or hardware features that result in IMD 14 being compatible with a more limited range of MRI modalities and/or MRI modality scan parameters. For example, a MRI conditionally safe device may be compatible with a limited range of magnetic field power levels or MRI radio frequency (RF) coil types. In either case, hardware features of an MRI safe or an MRI conditionally safe device may include construction of a housing of IMD 14, leads 16, any lead extensions or lead adaptors used, and/or circuitry within IMD 14. These hardware features may be designed to reduce or minimize inductive heating of components of IMD 14 or leads 16 when exposed to a magnetic field generated by an MRI modality. Additionally or alternatively, the hardware or software features may be designed to reduce or minimize electromagnetic interference between the magnetic field generated by the MRI modality and operation of IMD 14. It should be noted that an fMRI scan is a specialized MRI scan performed by an MRI unit. Thus, a device that is MRI safe or MRI compatible is also safe or compatible with an fMRI scan.

In some examples, IMD 14 has multiple modes, and is configured to enter a functional MRI mode, in which case IMD 14 may have any of the characteristics discussed above with respect to the MRI safe or an MRI conditionally safe device.

In accordance with one technique of the disclosure, IMD 14 may be placed in an fMRI mode that only allows unipolar, bipolar or multipolar stimulation arrangements. A bipolar stimulation arrangement generally refers to the use of an anode on a lead that sources current and a cathode on the same lead and/or another lead that sinks current. A multipolar stimulation arrangement generally refers to the use of more than one anode on a lead that each source current and one or more cathodes on the same lead or another lead that sink current, or the use of one anode on a lead that sources current and multiple cathodes on the same lead or another lead that sink current. In other words, in bipolar or multipolar stimulation arrangements, a case electrode on IMD 14 is not used to source or sink current. IMD 14 may also be placed in a unipolar mode specially adapted for fMRI scanning via the use of higher impedance connections to electrodes of leads 16, in line filters (e.g., filters in the electrical pathway from IMD 14 to the active electrodes), or other means. A unipolar stimulation arrangement generally refers to the use of an anode on a lead that sources current and a cathode on an outer housing of IMD 14 that sinks current, or the use of a cathode on the lead that sinks current and an anode on an outer housing of IMD 14 that sources current.

In addition, an fMRI mode may further include placing IMD 14 in a high impedance state for the duration of the fMRI scanning session. In another example, if placed in an fMRI mode, IMD 14 may perform a lead integrity check, e.g., lead impedance measurements, on leads 16A, 16B in order to ensure that there are no defects within the leads that may cause resonance at undesirable frequencies.

As shown in FIG. 1, leads 16 are implanted adjacent a spinal cord 18 of patient 12, e.g., for spinal cord stimulation (SCS) to alleviate pain. However, the techniques described in this disclosure are applicable to systems including an IMD 14 coupled to leads implanted to target any of a variety of target locations within patient 12, such as leads carrying electrodes located proximate to spinal cord 18, pelvic nerves, peripheral nerves, the stomach or other gastrointestinal organs, within the brain of patient 12, or other tissue sites (e.g., adjacent other nerves, muscles or muscle groups). In some examples, leads 16 may be coupled to lead extensions or lead adaptors.

In the example of FIG. 1, electrical stimulation energy is delivered from IMD 14 to spinal cord 18 of patient 12 via one or more electrodes carried by axial leads 16 (e.g., substantially cylindrical) implanted within patient 12, and, in some cases, one or more electrodes carried by IMD 14. In various applications, such as SCS, the adjacent implantable leads 16 may have longitudinal axes that are substantially parallel to one another. Various combinations of electrodes carried by the leads 16 may be used to deliver electrical stimulation, including combinations of electrodes on a single lead or combinations of electrodes on both leads. Also, in some examples, electrodes may be carried by paddle leads in which an array of electrodes may be arranged in a two-dimensional pattern, e.g., as columns or rows of electrodes, on a common planar lead surface.

For leads or other electrode arrays, electrodes may be formed as any of a variety of electrodes such as ring electrodes, segmented electrodes, needle electrodes, pad electrodes, or the like. In general, the term "electrode array" may refer to electrodes deployed on axial leads, paddle leads, or other lead configurations.

In the example of FIG. 1, leads 16 carry electrodes that are implanted adjacent to the target tissue of spinal cord 18. For example, leads 16 may be implanted in the epidural space adjacent spinal cord 18, and coupled to IMD 14. In the example of electrical FIG. 1, stimulation energy may be delivered to spinal cord 18 to eliminate or reduce pain perceived by patient 12. However, IMD 14 may be used with a variety of different therapies, such as peripheral nerve stimulation (PNS), peripheral nerve field stimulation (PNFS), deep brain stimulation (DBS), cortical stimulation (CS), pelvic floor stimulation, gastric stimulation, and the like. The stimulation may be configured to alleviate a variety of symptoms or conditions such as chronic pain, tremor, Parkinson's disease, movement disorders, psychological or mood disorders, epilepsy, urinary or fecal incontinence, sexual dysfunction, obesity, or gastroparesis. The stimulation delivered by IMD 14 may take the form of stimulation pulses or continuous waveforms, and may be characterized by controlled voltage levels or controlled current levels, as well as pulse width and pulse rate in the case of stimulation pulses.

The stimulation energy may be delivered via selected combinations of electrodes carried by one or both of leads 16. The target tissue may be any tissue affected by electrical stimulation energy, such as electrical stimulation pulses or waveforms. Such tissue may include nerves, nerve branches, smooth muscle fiber, and skeletal muscle fiber. In the example illustrated by FIG. 1, the target tissue is spinal cord 18. Stimulation of spinal cord 18 may, for example, prevent pain signals from traveling thorough the spinal cord and to the brain of patient 12. In some examples, patient 12 may perceive the interruption of pain signals as a reduction in pain and, therefore, efficacious therapy.

With reference to FIG. 1, a user, such as a clinician, physician or patient 12, may interact with a user interface of external programmer 20 to program IMD 14 or retrieve from IMD 14 information regarding operation of IMD 14. Programming of IMD 14 may refer generally to the generation and transfer of commands, programs, or other information to control the operation of the IMD 14. For example, programmer 20 may transmit programs, parameter adjustments, program selections, group selections, or other information to control the operation of IMD 14, e.g., by wireless telemetry. Parameter adjustments may refer to initial parameter settings or adjustments to such settings. A program may specify a set of parameters that define stimulation. A group may specify a set of programs that define different types of stimulation, which may be delivered simultaneously using pulses with independent amplitudes or on a time-interleaved basis.

As indicated above, programmer 20 may be a clinician programmer or a patient programmer. An example of a commercially available clinician programmer is the Medtronic N'Vision® Programmer Model 8840, marketed by Medtronic, Inc., of Minneapolis, Minn. An example of a commercially available patient programmer is the Medtronic myStim® Programmer, marketed by Medtronic, Inc. In some cases, external programmer 20 may be a physician or clinician programmer if it is primarily intended for use by a physician or clinician. In other cases, external programmer 20 may be a patient programmer if it is primarily intended for use by a patient.

In general, a physician or clinician programmer may support selection and generation of programs or parameters by a clinician for use by IMD 14. A clinician programmer may permit a clinician to control or adjust a larger set of therapy parameters than a patient programmer allows a patient to adjust. For example, a clinician programmer may allow a clinician to define new therapy programs or therapy parameter sets, or to modify parameters of an existing therapy program within a wide range, e.g., a parameter range accessible by hardware and/or software IMD 14. In contrast, a patient programmer may only allow a patient to select among predetermined therapy programs or to modify one or more therapy parameters within a range defined by the physician and programmed in the patient programmer, where the range is smaller than that available to the clinician programmer. In some examples, a patient programmer may be configured to be portable and carried by patient 12 during a daily routine. In some examples, a medical device system 10 may include both a patient programmer and a clinician programmer, which may enable a clinician to program IMD 14 and/or the patient programmer and may allow patient 12 some control over his or her therapy.

As discussed above, when IMD 14 cycles electrical stimulation therapy, IMD 14 delivers changes the stimulation parameters over time, e.g., resulting in different stimulation states. For example, IMD 14 can cycle electrical stimulation therapy by at least delivering stimulation according to one or more therapy programs in an alternating matter, according to each of a plurality of therapy programs in a linear (e.g., without any repeats) manner, such as in a predetermined order, according to two or more therapy programs in a repeating manner (e.g., a particular pattern), or the like. In some examples, IMD 14 automatically cycles electrical stimulation therapy, e.g., without human intervention. Programmer 20 may control IMD 14 when it cycles the stimulation therapy or a processor of IMD 14 may automatically control the cycling of electrical stimulation therapy. In other examples, IMD 14 cycles electrical stimulation therapy based on the input of a user, e.g., the user can provide input (e.g., via programmer 20) when a stimulation state change is desired, and the input can cause IMD 14 to switch stimulation states, thereby cycling stimulation therapy in one example.

In accordance with various techniques of this disclosure, external programmer 20 may be used to provide an indication (e.g., a notification) that IMD 14 is about to cycle or otherwise modify the electrical stimulation therapy being delivered. In other words, programmer 20 may provide an indication that IMD 14 is about to stop delivering electrical stimulation, e.g., for a predetermined amount of time in accordance with a therapy program or schedule, or that IMD 14 is about to deliver therapy according to another therapy program, e.g., having different electrode combinations, amplitude, pulse width (in examples in which IMD 14 generates and delivers stimulation pulses), or the like.

A processor of programmer 20 may determine the schedule with which IMD 14 cycles stimulation therapy between a plurality of stimulation states based on, for example, information about the schedule stored by programmer 20, IMD 14, or another device. A stimulation state may be characterized by, for example, the parameters (e.g., current or voltage amplitude, frequency, pulse width, electrode combination, and/or other parameters) with which electrical stimulation is generated and delivered by IMD 14, and in some examples, a stimulation state may be a state in which no electrical stimulation is being delivered to patient 12. In addition, clocks of IMD 14 and programmer 20 may be substantially synchronized in some examples such that programmer 20 may determine when a switch from one stimulation state to another by IMD 14 is imminent (e.g., is about to occur within about one second to about 5 seconds, although other time ranges are contemplated).

In some examples, the indication may be one or more of a textual notification, a graphical notification, an audible notification, and/or a somatosensory notification (e.g., a vibratory notification) provided by programmer 20. In such an implementation, an MRI operator may manually initiate an MRI scan of the patient via an MRI workstation based on the indication. In other examples, programmer 20 may be in communication with an MRI workstation. In such an implementation, the indication may be a sync or other signal that controls the MRI workstation to initiate an MRI scan of the patient in a master/slave relationship. Such a configuration may be desirable in order to reduce or eliminate the possibility of operator error. In some examples, the control of the MRI workstation by programmer 20 may be automatic, e.g., without user intervention, or may be semi-automatic, e.g., the MRI workstation may prompt a user in response to the signal from programmer 20, and the user may need to provide input to initiate an MRI scan.

In other cases, the indication may include information in addition to simple synchronization, such as the parameters with which the stimulator will begin stimulating at a specified time. This may allow the MRI workstation to appropriately document this information as an annotation or other association with the correlated scan. In addition or alternatively, this information, along with the fMRI scan data, may be stored together as part of an electronic medical record by a third system. In another example, programmer 20 may communicate the notification for display on the MRI workstation. These example implementations as well as other techniques for coordinating or synchronizing an fMRI scan with a change in electrical stimulation therapy are described in more detail below with respect to FIGS. 4-9, for example.

IMD 14 may be implanted in patient 12 at a location minimally noticeable to the patient. Alternatively, IMD 14 may be external to patient 12 and coupled to implanted leads via a percutaneous extension. For SCS, as an example, IMD 14 may be located, among other locations, in the lower abdomen, lower back, or other suitable location. In some examples, leads 16 may be tunneled from IMD 14 through tissue to reach the target tissue adjacent to spinal cord 18 for stimulation delivery. At distal portions of leads 16 are one or more electrodes (not shown) that transfer stimulation energy from the lead to the tissue adjacent the electrodes. The electrodes may be electrode pads on a paddle lead, circular (e.g., ring) electrodes that surrounding the entire outer perimeter of the respective lead 16, segmented (or partial-ring) electrodes arranged at different axial and rotational positions around a lead 12, conformable electrodes, cuff electrodes, or any other type of electrodes capable of forming unipolar, bipolar or multipolar electrode configurations.

In general, segmented electrodes arranged at selected axial and rotational positions at the distal ends of leads 16 will be described for purposes of illustration. But, the same systems and techniques may be used with therapy systems 10 that comprise other types of electrodes (e.g., ring electrodes or any of the other electrodes mentioned above).

IMD 14 delivers electrical stimulation to patient 12 via a subset of electrodes of leads 16 (and, in some cases, on an outer housing of IMD 14). This subset of electrodes may be referred to as an electrode combination. In the example of FIG. 1, each of the electrode combinations specifies a combination of electrodes arranged along lengths of two or more leads. If each lead 16 includes four ring electrodes, then the leads can be viewed as having four axial positions or levels. For segmented electrodes, an electrode may occupy a rotational arc at a given axial position of the lead. In some cases, the rotational arc may be similar to a portion of a ring electrode. For example, instead of a ring electrode that extends 360 degrees around an outer perimeter of a lead body, three, separate ninety degree segments could be provided to form three segmented electrodes at a given axial position along the length of the lead. Hence, two or more segmented electrodes may be provided at the same axial position but at different, non-overlapping rotational positions. Alternatively, a single segmented electrode could be provided at each of multiple axial levels. In general, in each case, a segmented electrode or electrode segment may have a dimension that spans only a portion of the outer perimeter (e.g., circumference in the case of a substantially cylindrical lead) of the lead, unlike a ring electrode which generally extends around the entire perimeter.

An electrode combination may include combinations of electrodes on the same lead or multiple leads, as well as one or more electrodes on a housing of IMD 14 in some cases. In each case, some electrodes in an electrode combination may form anodes while other electrodes form cathodes, establishing paths for flow of electrical stimulation current relative to an anatomical target, such as spinal cord nerve tissue at a desired position on the spinal cord. As an example, for SCS, stimulation may be delivered in the vicinity of the T7, T8 and T9 vertebrae, although other positions on the spinal cord are possible. In a current-based system, electrodes may be selected to form anodes or cathodes coupled to regulated current sources and sinks, respectively.

Figure 2:
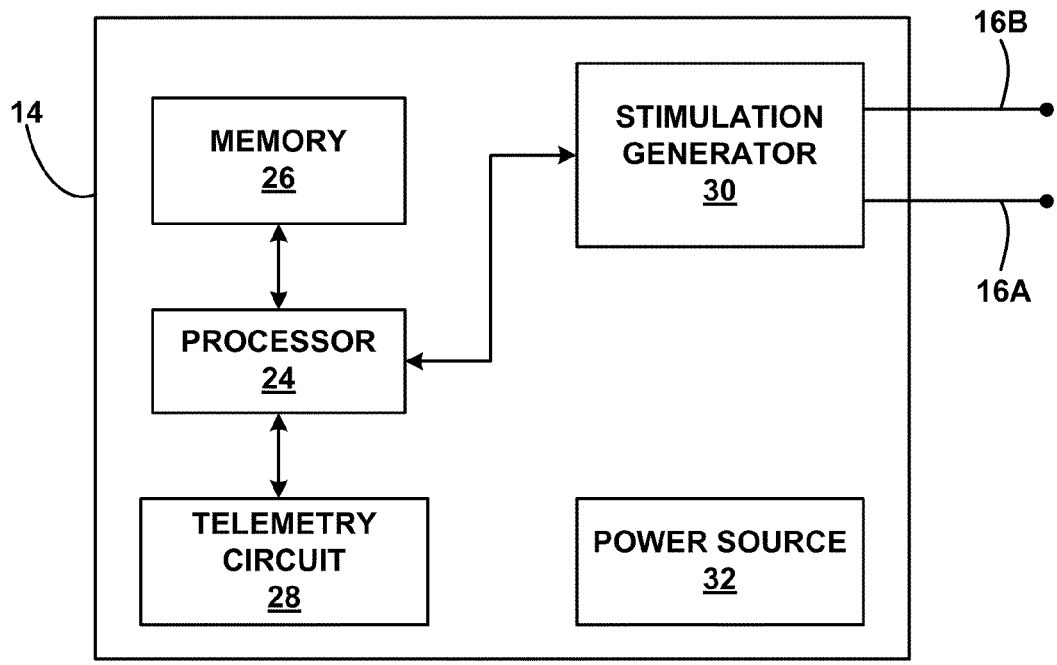
FIG. 2 is a functional block diagram illustrating various example components of an implantable electrical stimulation system.

FIG. 2 is a functional block diagram illustrating various components of an example IMD 14. In the example illustrated in FIG. 2, IMD 14 includes processor 24, memory 26, telemetry circuit 28, stimulation generator 30, and power source 32. Memory 26 may store instructions for execution by processor 24, stimulation therapy program data, sensor data, operational and status data, and any other electronic information regarding therapy or patient 12. Stimulation program data may include stimulation parameter values transmitted from programmer 20 and received by IMD 14, as well as programs defined by such parameter values, and, in some cases, program groups. Some data may be recorded for long-term storage and retrieval by a user. Memory 26 may include separate memories for storing different types of data.

In general, IMD 14 comprises any suitable arrangement of hardware, alone or in combination with software and/or firmware, to perform the techniques attributed to IMD 14 and processor 24, stimulation generator 30, and telemetry circuit 28 of IMD 14. In various examples, processor 24 can include any one or more microprocessors, digital signal processors (DSPs), application specific integrated circuits (ASICs), field programmable gate arrays (FPGAs), or any other equivalent integrated or discrete logic circuitry, as well as any combinations of such components. Memory 26 may any volatile or non-volatile media, such as a random access memory (RAM), read only memory (ROM), non-volatile RAM (NVRAM), electrically erasable programmable ROM (EEPROM), flash memory, and the like. Although processor 24, stimulation generator 30, and telemetry circuit 28 are described as separate modules, in some examples, processor 24, stimulation generator 30, and telemetry circuit 28 can be functionally integrated. In some examples, processor 24, stimulation generator 30, and telemetry circuit 28 correspond to individual hardware units, such as ASICs, DSPs, FPGAs, or other hardware units.

Processor 24 controls stimulation generator 30 to generate and deliver electrical stimulation via electrode combinations formed by electrodes in one or more electrode arrays. For example, stimulation generator 30 may deliver electrical stimulation therapy via electrodes of one or more leads 16, e.g., as stimulation pulses or continuous waveforms. Stimulation generator 30 may include stimulation generation circuitry to generate stimulation pulses or waveforms and, in some examples, switching circuitry to switch the stimulation across different electrode combinations, e.g., in response to control by processor 24. In particular, processor 24 may control the switching circuitry on a selective basis to cause stimulation generator 30 to deliver electrical stimulation to selected electrode combinations and to shift the electrical stimulation to different electrode combinations. In addition or instead, some examples, stimulation generator 30 may include multiple current or voltage sources to control delivery of stimulation energy to selected combinations of electrodes carried by leads 16.

Electrode combinations and other parameters associated with different therapy programs may be represented by data stored in a memory location, e.g., in memory 26, of IMD 14. Processor 24 may access the memory location to determine the electrode combination for a particular program and control stimulation generator 30 to deliver electrical stimulation via the indicated electrode combination. Each program may specify values for a set of stimulation parameters for delivery of electrical stimulation therapy. As an example, a program may specify electrode combination, electrode polarities, current or voltage amplitude, pulse rate and pulse width. Additional parameters such as duty cycle, duration, and delivery schedule also may be specified by a therapy program.

Using an external programmer, such as programmer 20, a user may select individual programs for delivery on an individual basis, or combinations of programs for delivery on a simultaneous or interleaved basis. In addition, a user may adjust parameters associated with the programs. The programs may be stored in memory 26 of IMD 14. In addition or instead, the programs may be stored in memory associated with external programmer 20. In either case, the programs may be selectable and adjustable to permit modification of therapy parameters. IMD 14 is configured to provide different stimulation states, which may be characterized by the stimulation delivered by IMD 14. Thus, IMD 14 may be in different stimulation states depending upon whether stimulation generator 30 is delivering stimulation to patient 12 or depending upon the program with which stimulation generator 30 is generating and delivering stimulation. In some examples, IMD 14 may be programmed to cycle between different stimulation states, e.g., between individual programs or combinations of programs. For example, processor 24 may control stimulation generator 30 to cycle between delivering electrical stimulation therapy to patient 12 in accordance with the parameters defined by a first program (e.g., stored by memory 26 of IMD 14 or a memory of another device, such as programmer 20) and not delivering electrical stimulation therapy. As an example, stimulation generator 30 may deliver the stimulation therapy according to a first program for about 30 seconds (a first stimulation state of IMD 14) and then turn off the stimulation therapy for about 30 seconds (a second stimulation state of IMD 14), and then deliver the stimulation therapy according to the first program for about 30 seconds (the first stimulation state of IMD 14), and so forth.

In another example, IMD 14 may cycle between combinations of therapy programs. For example, processor 24 may control stimulation generator 30 to cycle between delivering electrical stimulation therapy to the patient in accordance with parameter values defined by a first program (a first stimulation state of IMD 14) and delivering electrical stimulation therapy to the patient in accordance with parameter values defined by a second program (a second stimulation state of IMD 14). As an example, stimulation generator 30 may deliver the stimulation therapy according to the first program for about 30 seconds, then stimulation generator 30 may deliver the stimulation therapy according to the second program for about 30 seconds, then stimulation generator 30 may deliver the stimulation therapy according to the first program for about 30 seconds, and so forth. In some examples, an off state may be included. For instance, stimulation generator 30 may deliver the stimulation therapy according to the first program for about 30 seconds, and then stimulation generator 30 may not deliver any electrical stimulation for about 30 seconds. Thereafter, stimulation generator 30 may deliver the stimulation therapy according to the second program for about 30 seconds, and then stimulation generator may not deliver any electrical stimulation for about 30 seconds, and so forth.

IMD 14 may deliver electrical stimulation to patient 12 according to other therapy cycles. For example, stimulation generator 30 may deliver stimulation according to the first program, e.g., with frequency of 100 Hertz, then cycle to an off state, then deliver stimulation according to the second program, e.g., with frequency of 4 Hertz, then cycle to an off state. Stimulation parameters may be similar to therapeutic settings or they may be specially adapted for fMRI research purposes.

As discussed in further detail below, in some examples, it may be desirable for an MRI workstation to initiate a scan as soon as IMD 14 begins delivering electrical stimulation to patient 12. In other examples, it may be desirable for the MRI workstation to delay initiation of a scan by a predetermined or programmable delay period, even though IMD 14 is delivering stimulation to patient 12, in order to allow tissue, e.g., brain tissue, to achieve a therapeutic (or non-therapeutic, in the case of cessation of stimulation) state. The techniques described in this disclosure although coordination between the MRI workstation and IMD 14 regardless of the cycling pattern.

In some examples, programmer 20 (FIG. 1) may be a patient programmer, which may allow patient 12 to select among programs programmed by a clinician and stored in memory 26 of IMD 14 or the patient programmer. Additionally or alternatively, a patient programmer may allow patient 12 to adjust therapy parameters within a range determined by a clinician and stored in memory of the patient programmer or IMD 14. In addition, a physician programmer may permit generation of new programs, which may be loaded into memory 26 of IMD 14, and adjustment of parameters associated with existing programs.

Upon selection of a particular program or program group from memory 26, processor 24 may control stimulation generator 30 to deliver stimulation according to the programs in the groups, e.g., substantially simultaneously (e.g., partially overlapping stimulation signals) or on a time-interleaved basis. A group may include a single program or multiple programs, each of which specifies an electrode combination. Again, the electrode combination may specify particular electrodes in a single array or multiple arrays, e.g., on a single lead 16 or among multiple leads 16.

IMD 14 may be responsive to adjustments of programming parameters and electrode configurations by a user via programmer 20. In particular, processor 24 may receive adjustments to program parameters from programmer 20 via telemetry circuit 28. Telemetry circuit 28 may support wireless telemetry with external programmer 20 or another device by radio frequency (RF) communication, proximal inductive interaction of IMD 14 with external programmer 20, or other techniques. Telemetry circuit 28 may send information to and receive information from external programmer 20 on a continuous basis, at periodic intervals, or upon request from the stimulator or programmer. To support RF communication, telemetry circuit 28 may include appropriate electronic components, such as amplifiers, filters, mixers, encoders, decoders, modulators, demodulators and the like. In some examples, processor 24 also may communicate information to programmer 20 or another external device via telemetry circuit 28.

Power source 32 delivers operating power to the components of stimulator 14. Power source 32 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other embodiments, traditional non-rechargeable batteries may be used for a limited period of time. As a further alternative, an external inductive power supply could transcutaneously power IMD 14 when needed or desired.

Figure 3:
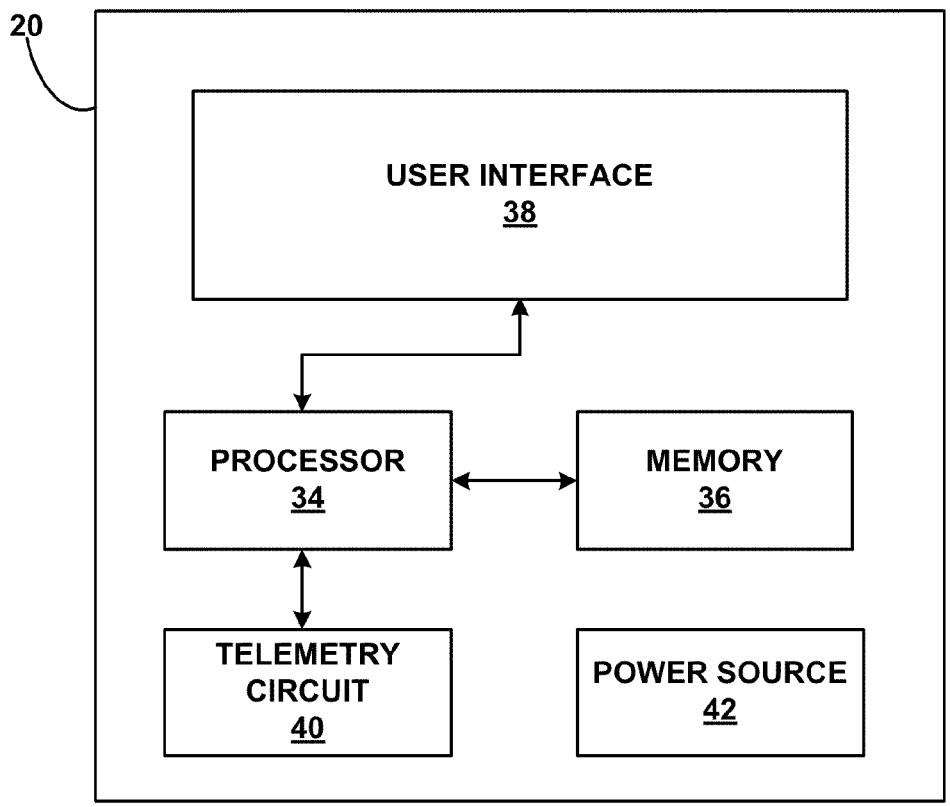
FIG. 3 is a functional block diagram illustrating various example components of an external programmer, such as a patient programmer or clinician programmer, which can be used to program therapy parameters and retrieve information from an implantable medical device.

FIG. 3 is a functional block diagram illustrating various components of an example external programmer 20, which is configured to communicate with and program IMD 14. As shown in FIG. 3, external programmer 20 includes processor 34, memory 36, user interface 38, telemetry circuit 40, and power source 42.

In general, programmer 20 comprises any suitable arrangement of hardware, alone or in combination with software and/or firmware, to perform the techniques attributed to programmer 20, and processor 34, user interface 38, and telemetry circuit 40 of programmer 20. In various examples, programmer 20 may include one or more processors, such as one or more microprocessors, DSPs, ASICs, FPGAs, or any other equivalent integrated or discrete logic circuitry, as well as any combinations of such components. Programmer 20 also, in various examples, may include a memory 36, such as RAM, ROM, PROM, EPROM, EEPROM, flash memory, a hard disk, a CD-ROM, a floppy disk, a cassette, magnetic media, or optical media comprising executable instructions for causing the one or more processors to perform the actions attributed to them. Moreover, although processor 34 and telemetry circuit 40 are described as separate modules, in some examples, processor 34 and telemetry circuit 40 are functionally integrated.

In some examples, external programmer 20 may be a patient programmer. A patient programmer may be portable and may be carried by patient 12 throughout his or her daily routine. A patient programmer may allow patient 12 to interact with user interface 38 to select programs, adjust program parameters, and retrieve information from IMD 14, e.g., on a limited basis as specified by the clinician. For example, the patient programmer may be configured to permit electrical stimulation amplitude, pulse width, or pulse rate adjustments to be made only within a limited range, or to permit only particular sets of electrode configurations to be selected by patient 12. In some examples, the patient programmer may allow patient 12 or other user to instruct the IMD 14 to enter an fMRI mode, which may configure the IMD 14 in a mode compatible with an fMRI scan.

In other examples, external programmer 20 may be a clinician programmer. In the case of a clinician programmer, a clinician interacts with user interface 38 in order to generate programs, adjust program parameters, such as voltage or current amplitude, pulse width, pulse rate, electrode combinations and electrode polarities. A clinician programmer may permit a clinician to control or adjust a larger, and perhaps complete, set of therapy parameters, relative to the limited set of parameters adjustable via a patient programmer. In some examples, the clinician programmer may allow the clinician or other user to instruct the IMD 14 to enter an fMRI mode, which may configure the IMD 14 in a mode compatible with an fMRI scan. In some examples, generation of programs and adjustment of program parameters may be aided by automated programming algorithms that guide the physician or clinician to select particular programs and program parameters.

In some examples, user interface 38 may include a display screen and one or more input buttons that allow external programmer 20 to receive input from a user. In some examples, the display may be, for example, a liquid crystal display (LCD), light emitting diode (LED) display, or a touch screen. The input buttons may include a touch pad, increase and decrease buttons, emergency shut off button, alphanumeric keypad or a reduced set of keys associated with particular functions, and/or other buttons needed to control the stimulation therapy. In some cases, the user may interact with user interface 38 via a stylus, soft keys, hard keys, directional devices, and any of a variety of other input media.

Processor 34 is configured to receive input from user interface 38, present data via user interface 38, retrieve data from memory 36 and store data within memory 36. Processor 34 also controls the transmission of data via telemetry circuit 40 to IMD 14. Memory 36 may include operational instructions for processor 34 or program parameter sets. For example, memory 36 may be a computer-readable storage medium comprising instructions that cause processor 34 to perform various functions.

Memory 36 may store information related to therapy system 10. For example, memory 36 may store information indicating a date on which IMD 14 and/or leads 16 were implanted in patient 12, a date on which any revision was made to IMD 14 and/or leads 16, or a name and/or phone number of a clinician who implanted IMD 14 or manages care of patient 12. In some examples, memory 36 may store a manufacturer of IMD 14 and contact information for the manufacturer, an identifier of IMD 14 and/or leads 16, such as a serial number, a model number, a registration number, or the like, or MRI scan settings to which IMD 14 safely can be exposed. Additionally or alternatively, memory 36 may store information regarding an implant location of IMD 14 and/or leads 16, a presence of another IMD implanted in patient 12, an indication of the presence of an abandoned, broken, or damaged lead 16, or an impedance of one or more of leads 16.

Telemetry circuit 40 allows the transfer of data to and from IMD 14. Telemetry circuit 40 may communicate automatically with telemetry circuit 28 of IMD 14 at a scheduled time or when the telemetry circuit detects the proximity of the stimulator. Alternatively, telemetry circuit 40 may communicate with IMD 14 or another device when signaled by a user through user interface 38. To support RF communication, telemetry circuit 40 may include appropriate electronic components, such as amplifiers, filters, mixers, encoders, decoders, modulators, demodulators and the like.

In some examples, telemetry circuit 40 may be used to retrieve information from memory 26 of IMD 14. For example, in response to an input from a user via user interface 38, processor 34 may transmit an instruction via telemetry circuit 40 to processor 24 of IMD 14 to retrieve information from memory 26 and transmit the information via telemetry circuit 28 to external programmer 20.

Power source 42 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

As mentioned above, fMRI is a technique that can be used to identify areas of neural activity in response to a stimulus. A patient that is deriving therapeutic effects from electrical stimulation can have different neural activity than a patient that is not deriving therapeutic effects from the electrical stimulation. As such, it may be desirable for a clinician to analyze the neural effects of electrical stimulation delivered via IMD 14, for example, via fMRI scans. A patient may be scanned while IMD 14 is cycling electrical stimulation between different stimulation states, e.g., alternating between delivering electrical stimulation according to a first program and not delivering therapy, or alternating between delivering stimulation therapy according to two or more programs. In some cases, IMD 14 may cycle electrical stimulation between a first program and a second program, where the first program is expected to be therapeutic for patient 12 (e.g., based on past testing on patient or similar subjects or based on clinician knowledge) and the second program is expected to be a non-therapeutic stimulation 12 (e.g., based on past testing on patient or similar subjects or based on clinician knowledge), which can be used as a control.

Due to restrictions on what may be in the MRI scanning room during scanning, changes to the patient's therapy programming (e.g., selecting the therapy that occurs during the therapy cycling) may be made between scans or IMD 14 can be programmed such that therapy is cycled periodically according to a predictable and known schedule. Because changing the therapy programming between scans may be burdensome and time consuming, e.g., the scan is stopped and patient 12 is moved out of the bore of the MRI unit in order to reprogram IMD 14, patients and clinicians may prefer that IMD 14 be programmed such that therapy is cycled periodically according to a schedule. However, in order to correlate each stimulation state with an fMRI scan, it may be necessary to coordinate changes to electrical stimulation therapy programs with fMRI scans. Coordination may be achieved by synchronizing a programmer (e.g., programmer 20) and IMD 14 and/or synchronizing a programmer and an MRI workstation, for example. Although various techniques are described throughout this disclosure with reference to fMRI, the techniques may also be applicable to other imaging modalities, e.g., MRI and positron emission topography (PET) scans.

Figure 4:
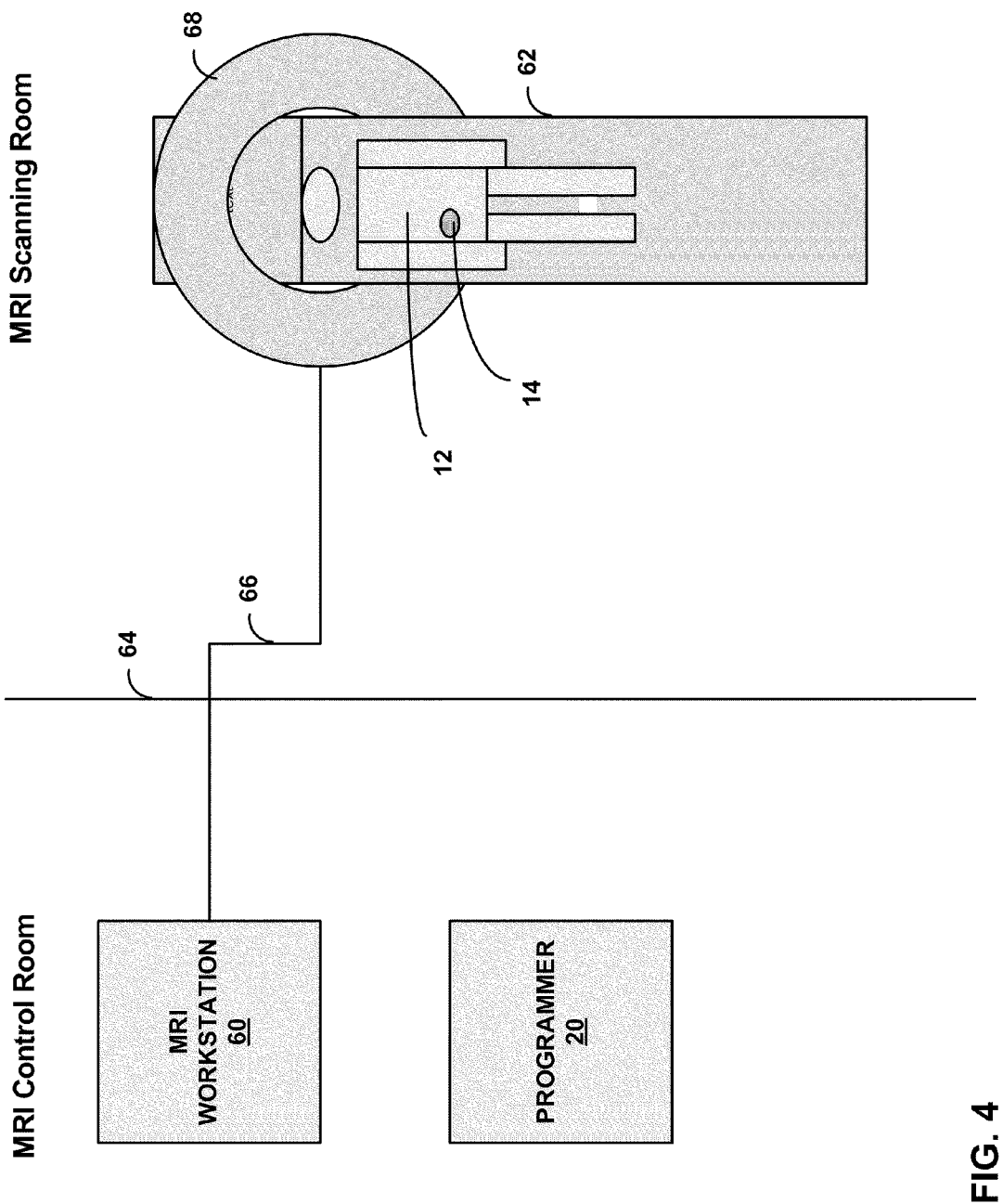
FIG. 4 is a block diagram illustrating an example system that may be used to coordinate changes in electrical stimulation therapy with a functional magnetic resonance imaging (fMRI) scan.

FIG. 4 is a block diagram illustrating an example system that may be used to coordinate changes in electrical stimulation therapy delivered by IMD 14, or different stimulation states of IMD 14, with an fMRI scan. In FIG. 4, external programmer 20 and MRI workstation 60 are located in an MRI control room and MRI unit 62, configured for performing fMRI scans on patient 12, is located in an MRI scanning room. The MRI control room and the MRI scanning room are separated by wall 64 in the example shown in FIG. 4. MRI workstation 60 is in electrical communication with MRI unit 62 via control line 66. It should be noted that only a portion of bore 68 of MRI unit 62 is shown in FIG. 4.

As seen in FIG. 4, patient 12 has been fitted with an MRI safe or an MRI conditionally safe IMD 14. Although referred to as an implantable medical device, IMD 14 may be, in some example implementations, an external trial stimulator, as discussed in more detail below.

In some examples of the implementation depicted in FIG. 4, prior to initiating an fMRI scan of patient 12, programmer 20 programs IMD 14 to enter a cycling and scheduling mode, in which stimulation generator 30 (FIG. 2) of IMD 14 cycles through two or more stimulation states (e.g., cycles between therapy programs stored in memory 26 (FIG. 2) of IMD 14 or cycles between one or more programs and periods of in which no electrical stimulation is delivered to patient 12) according to a predetermined and stored schedule. In one example, in the cycling and scheduling mode, IMD 14 delivers electrical stimulation to patient 12 according to a first program, then stops delivery of all electrical stimulation to patient 12, then delivers electrical stimulation according to the first program again, and so forth, in a predictable manner as set forth by the predetermined schedule. In another example, IMD 14 may deliver electrical stimulation to patient 12 according to a first program, and then stop delivery of all electrical stimulation to patient 12, then deliver stimulation to patient 12 according to a second program, then stop delivery of all electrical stimulation to patient 12, then deliver electrical stimulation according to a first program, then stop, and so forth, in a predictable manner as set forth by the schedule. In each of these examples, IMD 14 cycles between two or more stimulation states.

In other examples, IMD 14 may deliver electrical stimulation to patient 12 according to a first program, then stop delivery of all electrical stimulation to patient 12, then gradually increase or decrease the current or voltage amplitude, e.g., ramp the amplitude up or down, then stop delivery of all electrical stimulation to patient 12, in a predictable manner as set forth by the schedule. These examples are not meant to be exhaustive. Rather, the examples are meant to enhance the reader's understanding of what is meant by cycling of electrical stimulation therapy. In other examples, there may be more than two electrical stimulation programs delivered via a schedule, delivery of electrical stimulation may not be stopped before changing to another stimulation program or changing stimulation parameter values, or other modifications can be made to the cycled stimulation states. IMD 14 may signal, via its telemetry circuitry 28 (FIG. 2) or other means (audible beeper), when it is about to begin a stimulation change (e.g., a change in the stimulation state) in order to aid synchronization with the MRI scanning sequence controlled by MRI workstation 60.

Once programmer 20 has programmed IMD 14 to enter a mode in which one or more therapy programs are cycled in a predictable manner, e.g., according to a schedule, programmer 20 is removed from the MRI scanning room. During fMRI scanning, programmer 20 may be used by an operator operating MRI workstation 60 in the MRI control room in order to coordinate changes to electrical stimulation therapy programs with fMRI scans.

As indicated above, IMD 14 may be programmed to enter a mode in which the cycling of one or more programs occurs in a predictable manner set forth by a schedule. Although not configured in a master/slave relationship with IMD 14, programmer 20 can be synchronized with IMD 14 via programming such that any changes to the electrical stimulation delivered to patient 12 by IMD 14 are indicated by programmer 20 to the operator of MRI workstation 60. For example, programmer 20 may provide, via user interface 38 (FIG. 3), an indication (e.g., a graphical notification, a textual notification, a numerical notification, an audible notification, and/or a somatosensory notification) that IMD 14 is about to change stimulation states, e.g., from one program (defining one set of stimulation parameter values) to another program (defining a different set of stimulation parameter values) including an "off" state in which no stimulation is being delivered to patient 12. As another example, programmer 20 may communicate the notification for display or other presentation on a remote device, such as MRI workstation 60.

The indication that IMD 14 is about to change stimulation states can take any suitable format. In one example, the indication includes a color coded graphical notification. For example, different colors may blink or be displayed via a display of programmer 20 or MRI workstation 60 to indicate, to the operator, a change in stimulation state of IMD 14 will occur or has occurred. In another example, the indication comprises an alphanumeric notification that provides a countdown to the change in the stimulation state, e.g., in seconds. The countdown can be, for example, textual or numerical (e.g., a display of a number of seconds remaining before IMD 14 changes stimulation state), or some other time-based countdown.

In another example, the indication provided to the operator via programmer 20 or workstation 60 may not only indicate that a particular stimulation state is beginning, but indicate the stimulation level. For example, the indication may indicate that stimulation is beginning, increasing to 25%, increasing to 50%, increasing to 75%, and finally stimulation is at 100% of the programmed stimulation intensity of a particular program, such that the indication reflects a ramping up of stimulation. Likewise, the indication may reflect a ramping down of stimulation.

In other examples, user interface 38 (FIG. 3) of programmer 20 may comprise a speaker. The speaker may provide an audible signal to the operator that indicates IMD 14 will change stimulation states, or provide some other audible notification. Similarly, in some examples, user interface 38 may comprise a mechanism that provides a somatosensory alert, and processor 24 may control the mechanism to vibrate, e.g., in a particular pattern or just vibrate, to indicate that IMD 14 will change stimulation states. In each of these examples, the indication may be provided a known period of time prior to the change in stimulation state of IMD 14, such as about one second to about 30 seconds prior to IMD 14 switching between programs or prior to IMD 14 turning electrical stimulation off.

In another example implementation, IMD 14 or another device configured to deliver electrical stimulation therapy, such as an external trial stimulator, may generate an indication indicative of an imminent change in stimulation state in addition to or instead of programmer 20 and/or MRI workstation 60. For instance, IMD 14 or an external trial stimulator may generate a sequence of alert beeps prior to changing stimulation state. In some instances, the sequence of alert beeps may be generated when the device is placed in an fMRI mode as such alerts on a chronic basis may be undesirable.

Once notified by programmer 20 that IMD 14 is changing stimulation states, the operator may provide input to MRI workstation 60 to initiate another scan of patient 12. For example, upon seeing a countdown reach zero on user interface 38 of programmer 20, the operator may press a button or signal via some other input mechanism on MRI workstation 60 to begin a scan of patient 12. In this way, the operator may coordinate changes in electrical stimulation therapy programs (or other stimulation states) delivered via IMD 14 with fMRI scans based on the indication from programmer 20, workstation 60, and/or IMD 14 or another device, which may allow each stimulation state to be associated with an fMRI scan that was taken at the time IMD 15 was in the particular stimulation state.

In another example implementation, rather than delivering electrical stimulation to patient 12 according to a predetermined schedule, IMD 14 enters one or more stimulation states based on detection of MRI activation. Detection of an MRI activation may indicate, for example, that a scan has been started. IMD 14 can comprise a sensor, e.g., a Hall effect sensor, a reed switch or the like, capable of detecting MRI activation, or a sensor physically separate from IMD 14 can be implanted or carried external to patient 12 to detect the MRI activation. A processor of IMD 14 (or another device) can detect the MRI activation, for example, based on the output of a sensor (e.g., a signal output by the sensor) that indicates a presence of a relatively high magnetic field (e.g., about 0.5 Tesla to about 5.0 Tesla). Upon detecting MRI activation via the sensor, processor 24 (FIG. 2) of IMD 14 may cycle or toggle stimulation states, or shift to the next stimulation regime in a sequence. In this way, each fMRI scan may be associated with a respective stimulation state of IMD 14. Such an implementation may allow fMRI scans to happen asynchronously, but, nevertheless, be associated with known stimulation states.

In another example implementation, a user, such as the MRI operator or other clinician, may manually control programmer 20 to change the stimulation state of IMD 14, e.g., the user changes stimulation programs or stimulation parameters. Then, programmer 20 may automatically transmit an indication to MRI workstation 60, and the operator can initiate a new scan upon receiving the notification, as discussed above.

In another example, fMRI scanning can be coordinated with the stimulation delivered by IMD 14 based on a synchronization signal transmitted by IMD 14 to programmer 20, where the signal indicates an imminent or a recently implemented change in stimulation state of IMD 14. This may be useful in some examples, such as in examples in which IMD 14 is capable of changes that are asynchronous and, thus, unpredictable to an outside instrument (e.g., programmer 20 or workstation 60). For example, in some examples, IMD 14 controls stimulation to patient 12 based on a detected patient state. Example patient states include, but are not limited to, a sleep state, a movement state, a seizure state in which one or more symptoms of a seizure are observed, or a mood state in which one or more symptoms of a psychological disorder are observed. The patient state can be detected, for example, based on one or more physiological parameters sensed by IMD 14 or a sensor in communication with IMD 14. The physiological parameter can be, for example, brain activity (e.g., sensed via electroencephalogram (EEG) or electrocorticogram (ECoG)), muscle activity (e.g., sensed via an electromyogram), body temperature (e.g., sensed via thermal sensing electrodes), cardiac activity (e.g., sensed via an electrocardiogram (ECG)), brain activity (e.g., sensed via an EEG or ECoG), electrodermal activity, or respiratory activity.

As an example, processor 24 (FIG. 2) of IMD 14 may be configured to select a program for controlling stimulation therapy to patient 12 based on a determined patient state. Upon detecting a particular patient state and selecting a program associated with the patient state (e.g., associated in memory 26), processor 24 can control telemetry circuitry 28 to transmit a signal to programmer 20 to indicate imminent delivery of stimulation according to the selected program. Programmer 20 may then transmit an indication to MRI workstation 60 or the operator of MRI workstation 60 either directly in examples in which programmer 20 can communicate directly with MRI workstation 60, or indirectly via an intermediate device, where the indication indicates that IMD 14 is about to change stimulation states (e.g., within a predetermined amount of time) or has switched stimulation states. MRI workstation 60, alone or in response to input from an operator, can then begin the fMRI scan upon receiving the indication from IMD 14 (directly or indirectly via programmer 20).

As an example of how the fMRI scan can be coordinated with a particular stimulation state of IMD 14 even when IMD 14 delivers asynchronous stimulation, IMD 14 may be configured to initiate delivery of stimulation to patient 12 when seizure or other epileptic activity is detected, e.g., based on a sensed EEG or ECoG signal. In these examples, processor 24 of IMD 14 may send a signal to programmer 20 at the onset of the stimulation in order to, for example, enable an operator or the MRI workstation 60 to coordinate the start of the fMRI scan in time to catch stimulation effects. When the seizure or other epileptic activity is detected, processor 24 of IMD 14 may, for example, select a specific program associated with the detected activity in memory 26, and control stimulation generator 30 to generate and delivery stimulation to patient 12 according to the selected program. In some examples, processor 24 of IMD 14 may send a signal to programmer 20 that indicates the program in order to, for example, enable an operator of MRI workstation 60 to associate the fMRI scan with the program.

Each of the techniques and systems described above result in an fMRI scan being associated with a respective stimulation state of IMD 14, which may enable the effects of the stimulation state to be determined at a later time based on the associated fMRI scan. The fMRI scans may be correlated with the stimulation state (e.g., delivered stimulation programs and/or stimulation parameter values) in any one or more of a number of suitable ways. For example, an operator may manually record the time when an fMRI scan has been initiated and match up the times of the stimulation states (e.g., stored by IMD 14) with the fMRI scans. In other examples, a correlation may be stored in memory 26 of IMD 14 and/or memory 36 of programmer 20. In other examples, the fMRI scans may be marked or annotated (e.g., via workstation 60) with data that identifies information related to the stimulation program and/or stimulation parameters.

Figure 5:
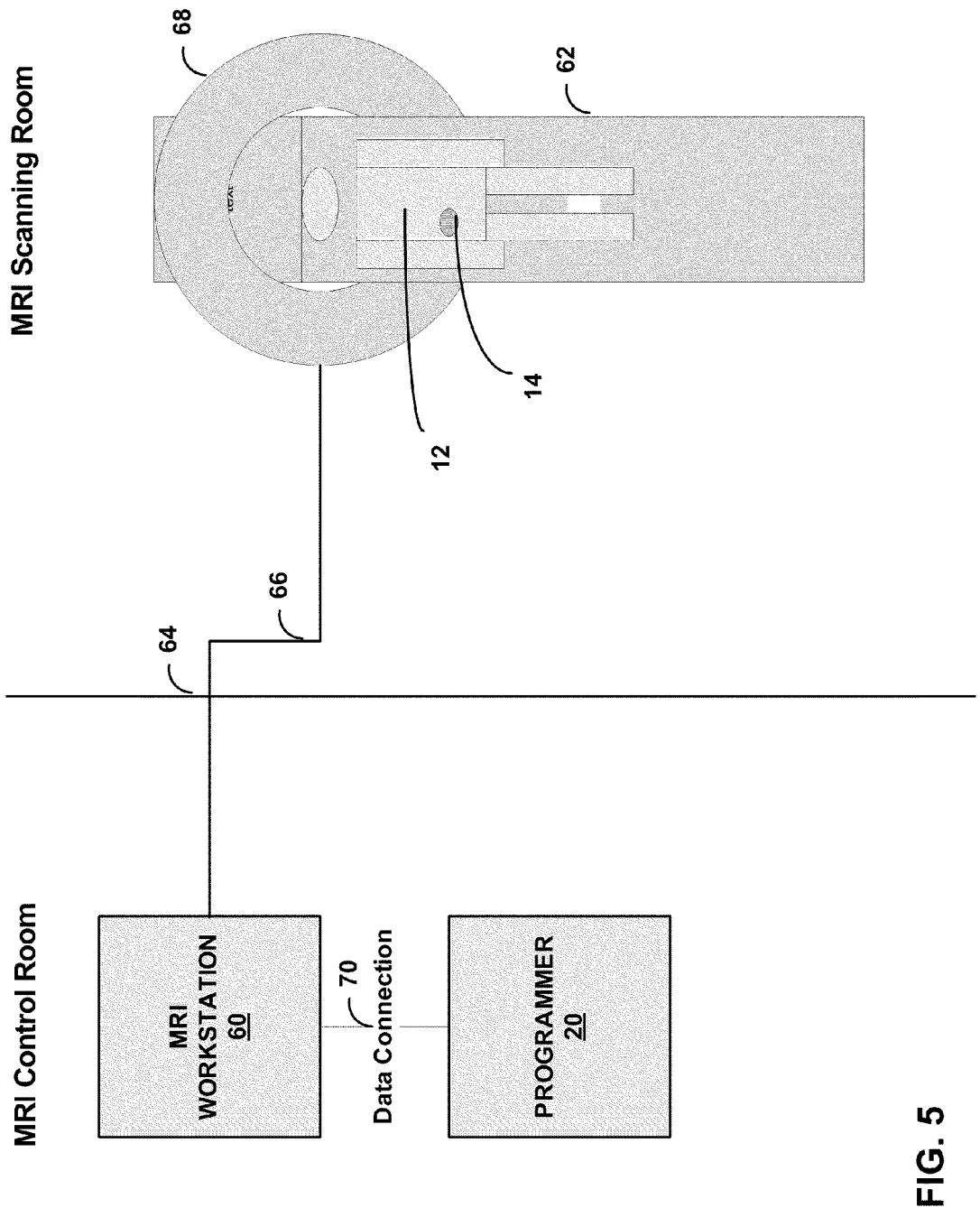
FIG. 5 is a block diagram illustrating another example system that may be used to coordinate changes in electrical stimulation therapy with an fMRI scan.

FIG. 5 is a block diagram illustrating another example system that may be used to coordinate changes in electrical stimulation therapy with an fMRI scan. FIG. 5 is similar to FIG. 4 and, for purposes of conciseness, only the differences between FIG. 5 and FIG. 4 will be described below. In FIG. 5, programmer 20 is in communication with MRI workstation 60 via data connection 70. In this example implementation, programmer 20 directly communicates any changes in electrical stimulation therapy delivered by IMD 14 to MRI workstation 60. Such an implementation may be advantageous in that it may reduce or even eliminate the need for an operator to manually initiate an fMRI scan based on a visual, audible, or other notification provided by programmer 20, as in FIG. 4. Instead, MRI workstation 60, upon receipt of a sync trigger or other signal, MRI workstation 60 may automatically, i.e., without user intervention, initiate (or begin) the next fMRI scan. In this manner, programmer 20 and MRI workstation 60 can operate in a master/slave relationship.

Data connection 70 may be a hardwired connection, a network connection, wireless connection, or some other connection that allows programmer 20 to communicate information in real time such that when programmer 20 determines that a change in a stimulation state is occurring, programmer 20 may signal to the MRI workstation to begin a scan.

In some example implementations, rather than starting and stopping fMRI scanning, scanning may be continuous. In such an implementation, programmer 20 may communicate, via data connection 70, the current stimulation state to MRI workstation 60 and MRI workstation 60 may annotate or otherwise "mark" the fMRI scans, e.g., individual frames, based on the current stimulation state. Later, the fMRI scans and stimulation states may be post-correlated for analysis using the time-stamps.

Figure 6:
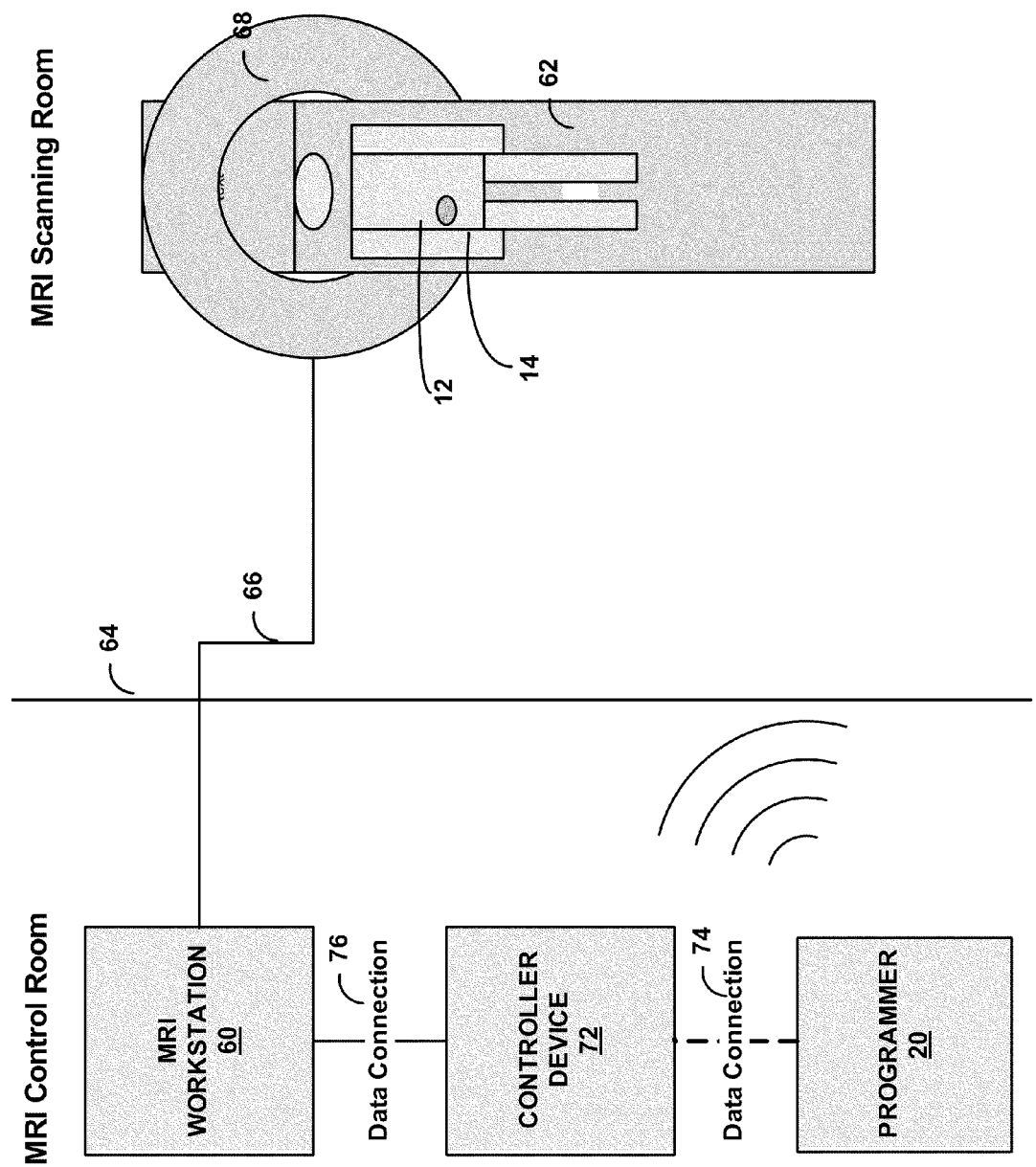
FIG. 6 is a block diagram illustrating another example system that may be used to coordinate changes in electrical stimulation therapy with an fMRI scan.

FIG. 6 is a block diagram illustrating another example system that may be used to coordinate changes in electrical stimulation therapy with an fMRI scan. Unlike the example depicted in FIG. 5, FIG. 6 depicts programmer 20 in communication with controller device 72 via data connection 74 and controller device 72 in communication with MRI workstation 60 via data connection 76. As such, controller device 72, e.g., a laptop computer or another computing device, may provide protocol coupling between programmer 20 and MRI workstation 60. In some examples, programmer 20 and MRI workstation 60 may be configured to communicate via different protocols. In these examples, controller device 72, which can be configured to communicate via both protocols, may act as an intermediate device that enables programmer 20 and MRI workstation 60 to communicate with each other.

In some examples, data connection 74 may be a wireless connection between programmer 20 and controller device 72 and, as such, is depicted as a dotted line. However, in other example implementations, data connection 74 may be a hardwired connection, a network connection, or some other connection that allows information to be communicated in real time between programmer 20 and controller device 72. Controller device 72 is in communication with MRI workstation 60 via data connection 76. Data connection 76 may also be a hardwired connection, a network connection, or some other connection that allows information to be communicated in real time between controller device 72 and MRI workstation 60.

In FIG. 6, controller device 72 controls both MRI workstation 60 and programmer 20. For example, controller device 72 can be configured to transmit a signal to MRI workstation 60, via data connection 76, that causes MRI workstation 60 to control MRI unit 62 to begin a scan. Instead or in addition, controller device 72 can be configured to transmit a signal to programmer 20, via data connection 74, that causes programmer 20 to initiate, via IMD 14, a particular stimulation state (e.g., initiate electrical stimulation according to a particular program or pause all electrical stimulation). In other words, in the example shown in FIG. 6, controller device 72 is the master and both MRI workstation 60 and programmer 20 are slaves. For example, controller device 72 may begin a countdown and when the countdown reaches zero, controller device 72 communicates a "begin scan" signal to MRI workstation 60 as well as a "initiate stimulation" signal to programmer 20. Upon receiving the "begin scan" signal, MRI workstation 60 may begin an fMRI scan of patient 12. Upon receiving the "initiate stimulation" signal, programmer 20 may transmit a signal to IMD 14 indicating that the IMD 14 should begin delivering electrical stimulation therapy in accordance with one or more therapy programs. In some cases, programmer 20 may transmit the program parameters to IMD 14 and IMD 14 may begin delivering stimulation according to the received parameters.

In some examples, controller device 72 may use Medical Implant Communication Service (MICS) band telemetry to initiate device protocol such that IMD 14 will be synchronized to fMRI scanning. In this scenario, a user may cause programmer 20 to signal IMD 14 to change stimulation states synchronous with his or her observation of the beginning of a scan. Because distance telemetry between programmer 20 and IMD 14 may be able to function without needing equipment in the MRI scanning room, the stimulation delivered by IMD 14 can be made responsive to the fMRI scanning protocol. In this example, programmer 20 is capable of distance communication with IMD 14, thereby allowing programmer 20 to initiate the stimulation regime. For example, telemetry circuit 40 of programmer 20 may be configured for distance telemetry.

In other examples, the fMRI scanning can be coordinated with the stimulation delivered by IMD 14. IMD 14 configured for such distance telemetry with programmer 20 may, for example, send a synchronization signal to programmer 20 in advance of stimulation changes. This may be useful in some examples, such as in examples in which IMD 14 is capable of changes that are asynchronous and, thus, unpredictable to an outside instrument (e.g., programmer 20, controller device 72, or workstation 60). As discussed above, for example, in some configurations, processor 24 (FIG. 2) of IMD 14 selects a program for controlling stimulation therapy to patient 12 based on a determined patient state. IMD 14 may transmit a signal to programmer 20 to indicate imminent delivery of stimulation according to a selected program, and programmer 20 may then transmit an indication to MRI workstation 60 or the operator of MRI workstation 60, either directly in examples in which programmer 20 can communicate directly with MRI workstation 60, or indirectly via controller device 72. In examples in which controller device 72 communicates a "begin scan" signal to MRI workstation 60, device 72 may communicate the "begin scan" signal upon receiving an indication from IMD 14 (directly or indirectly via programmer 20) that IMD is about to change stimulation states.

In some examples, the system in FIG. 6 may further include an MRI safe telemetry extender (not shown) that extends from outside bore 68 to inside bore 68 of MRI unit 62 in order to allow programmer 20 to communicate with IMD 14.

In some examples, the "begin scan" signal transmitted from controller device 72 to MRI workstation 60 may not indicate that a scan should begin immediately upon receipt of the signal. Rather, the "begin scan" signal may include a countdown or other time-based indicator that provides some indication to MRI workstation that a scan should begin at the end of the countdown. A similar feature may be included in the "initiate stimulation" signal sent from controller device 72 to programmer 20. The "initiate stimulation" signal may, for example, prime IMD 14 to initiate a particular stimulation program or cycle the next time IMD 14 or a separate sensor observes the MRI magnetic field.

Figure 7:
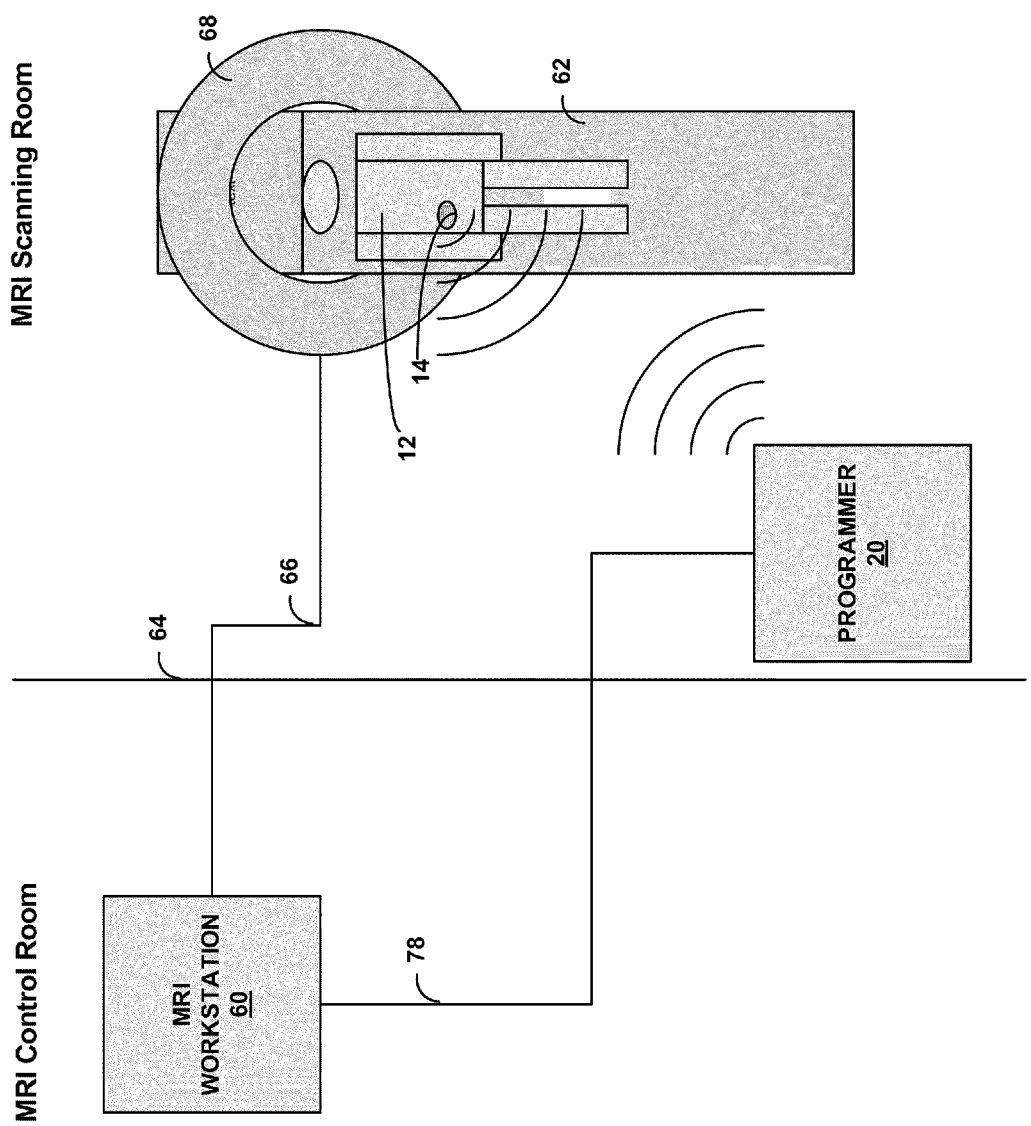
FIG. 7 is a block diagram illustrating another example system that may be used to coordinate changes in electrical stimulation therapy with an fMRI scan.

FIG. 7 is a block diagram illustrating another example system that may be used to coordinate changes in electrical stimulation therapy with an fMRI scan. In FIG. 7, MRI workstation 60 is located in an MRI control room while MRI unit 62, which is configured to perform fMRI scans on patient 12, and external programmer 20, which is MRI safe in the example shown in FIG. 7, are located in an MRI scanning room. The MRI control room and the MRI scanning room are separated by wall 64. MRI workstation 60 is in electrical communication with MRI unit 62 via control line 66. In addition, MRI workstation 60 is in electrical communication with programmer 20 via control line 78, e.g., TTL serial communication cable.

In the example system shown in FIG. 7, MRI workstation 60 transmits a signal to programmer 20 to reprogram IMD 14, or otherwise change the electric stimulation therapy delivered to patient 12 by IMD 14. In response to receiving the signal from MRI workstation 60, programmer 20 transmits, via telemetry circuit 40, information to IMD 14 to actuate the requested change in electrical stimulation therapy. IMD 14 receives the information via telemetry circuit 28 (FIG. 2) and modifies the delivery of electrical stimulation accordingly. In this manner, MRI workstation controls programmer 20 in a master/slave relationship, thereby providing synchronization between programmer 20 and MRI workstation 60.

Programmer 20 is capable of distance communication with IMD 14, thereby allowing programmer 20 to initiate, or in the case where IMD 14 signals impending changes, to detect the stimulation regime. For example, telemetry circuit 40 (FIG. 3) of programmer 20 may be configured for distance telemetry. In addition, the system in FIG. 7 may further include an MRI safe telemetry extender (not shown) that extends from outside bore 68 to inside bore 68 of MRI unit 62 in order to allow programmer 20 to communicate with IMD 14.

Figure 8:
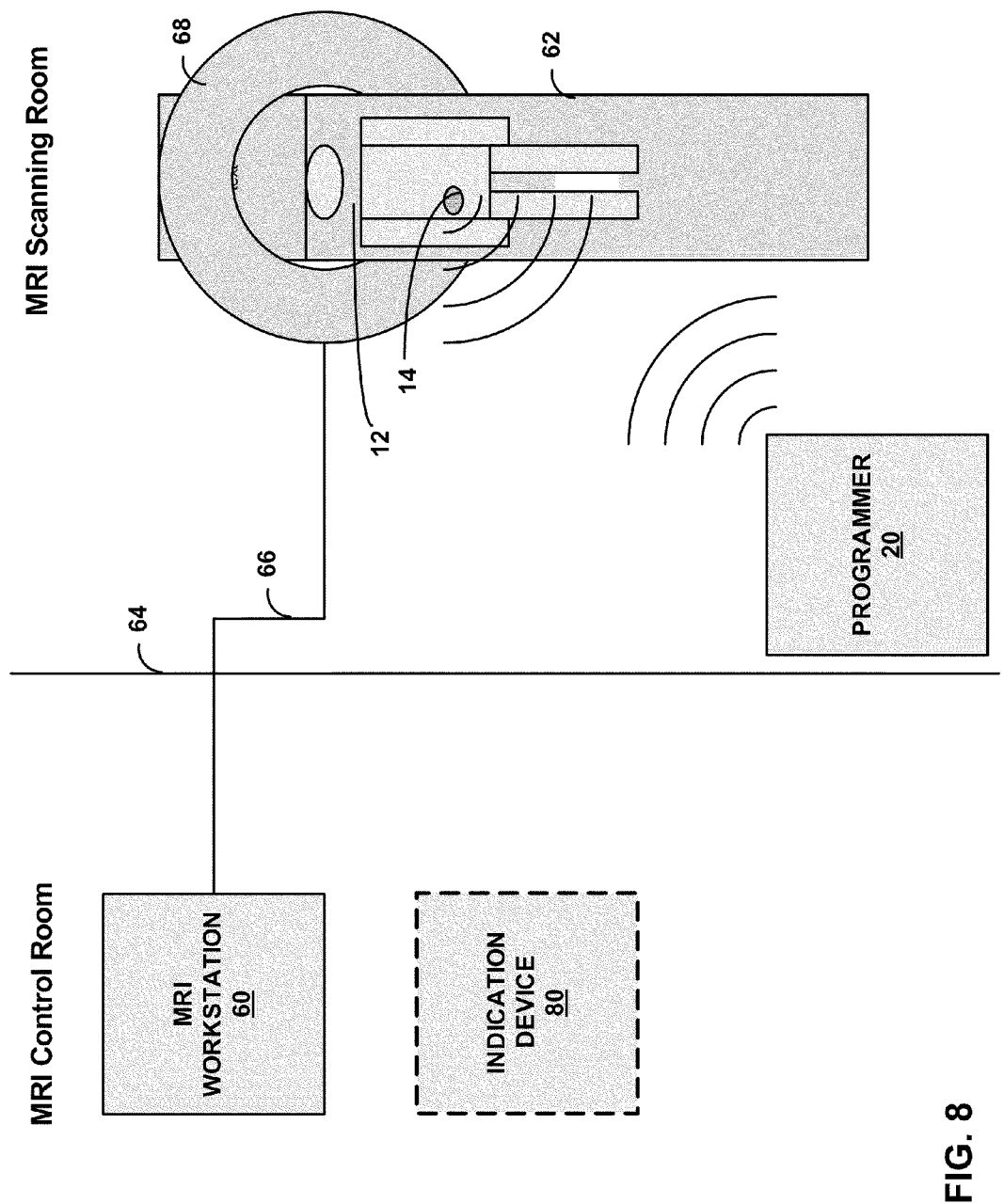
FIG. 8 is a block diagram illustrating another example system that may be used to coordinate changes in electrical stimulation therapy with an fMRI scan.

FIG. 8 is a block diagram illustrating another example system that may be used to coordinate changes in electrical stimulation therapy with an fMRI scan. In FIG. 8, MRI workstation 60 is located in an MRI control room, and MRI unit 62, used for performing fMRI scans on patient 12, and external programmer 20, which is MRI safe in the example shown in FIG. 8, are located in an MRI scanning room. The MRI control room and the MRI scanning room are separated by wall 64. Like the example depicted and described above with respect to FIG. 4, an operator operating MRI workstation 60 can manually begin an fMRI scan of patient 12 based upon receiving an indication that IMD 14 is about to change stimulation states (e.g., within a predetermined amount of time, such as about 30 seconds or less). In FIG. 8, the indication is provided to the operator by indication device 80 located within the MRI control room. In some examples, indication device 80 may be a laptop computer. Any of the notifications described above with respect to FIG. 4 can also be provided by indication device 80 to indicate that IMD 14 is about to change stimulation states.

Programmer 20 is configured to reprogram IMD 14, or otherwise change the electrical stimulation therapy delivered to patient 12 by IMD 14, according to predefined schedule. In order to reprogram IMD 14, programmer 20 is capable of distance communication with IMD 14. For example, telemetry circuit 40 (FIG. 3) of programmer 20 may be configured for distance telemetry. In addition, the system in FIG. 8 may further include an MRI safe telemetry extender (not shown) that extends from outside bore 68 to inside bore 68 of MRI unit 62 in order to allow programmer 20 to communicate with IMD 14.

Indication device 80 is synchronized with IMD 14 such that any changes to the electrical stimulation delivered to patient 12 by IMD 14 are indicated by indication device 80 to the operator of MRI workstation 60. For example, indication device 80 may include a stimulation-specific stopwatch that provides a time base that is synchronized with stimulation states of IMD 14. For example, when programmer 20 initiates stimulation delivery by IMD 14 according to a particular set of stimulation programs (e.g., in a cycling manner), the stopwatch running on indication device 80 may be synchronized with the stimulation programs delivered by IMD 14, such that indication device 80 may provide an indication to the operator of MRI workstation 60 that IMD 14 has switched between stimulation states (e.g., between programs or between a program and a no-stimulation state) or such a switch is imminent. For example, indication device 80 may provide the operator with a countdown or other notification that guides the operator to begin a fMRI scan of patient 12 at an appropriate time (e.g., at the start of a new stimulation state of IMD 14).

Indication device 80 may provide a graphical notification, a textual notification, a somatosensory notification, a numerical notification, an audible notification, and/or any other suitable notification that indicates IMD 14 is about to change stimulation states. The stimulation state change may be, for example, from one program to another program, or from one program to an "off" state in which no stimulation is being delivered to patient 12.

In order to help synchronize the indications with the stimulation delivery by IMD 14, indication device 80 may receive, as inputs, any parameters that may affect the timing of stimulation. For example, indication device 80 may receive the length of the stimulation program, e.g., 30 seconds. Indication device 80 may receive the time between delivering therapy according to a first program and delivering therapy according to a second program, e.g., 5 seconds. Indication device 80 may also receive any programmable delays that are necessary in some stimulation regimes for the affects of the electrical stimulation on tissue to be observed. Indication device 80 may further receive ramp up or ramp down times that may affect time. A number of other parameters may be useful in order for the stopwatch on indication device 80 to synchronize with IMD 14, such as the stimulation rates and the widths or shapes of given stimulation pulses of a particular program. Indication device 80 may receive these parameters in a number of different ways. For example, the parameters may be manually entered via a user interface of indication device 80, imported via a synchronization file exported by programmer 20, communicated via network, or imported from an electronic medical record stored in programmer 20.

Figure 9:
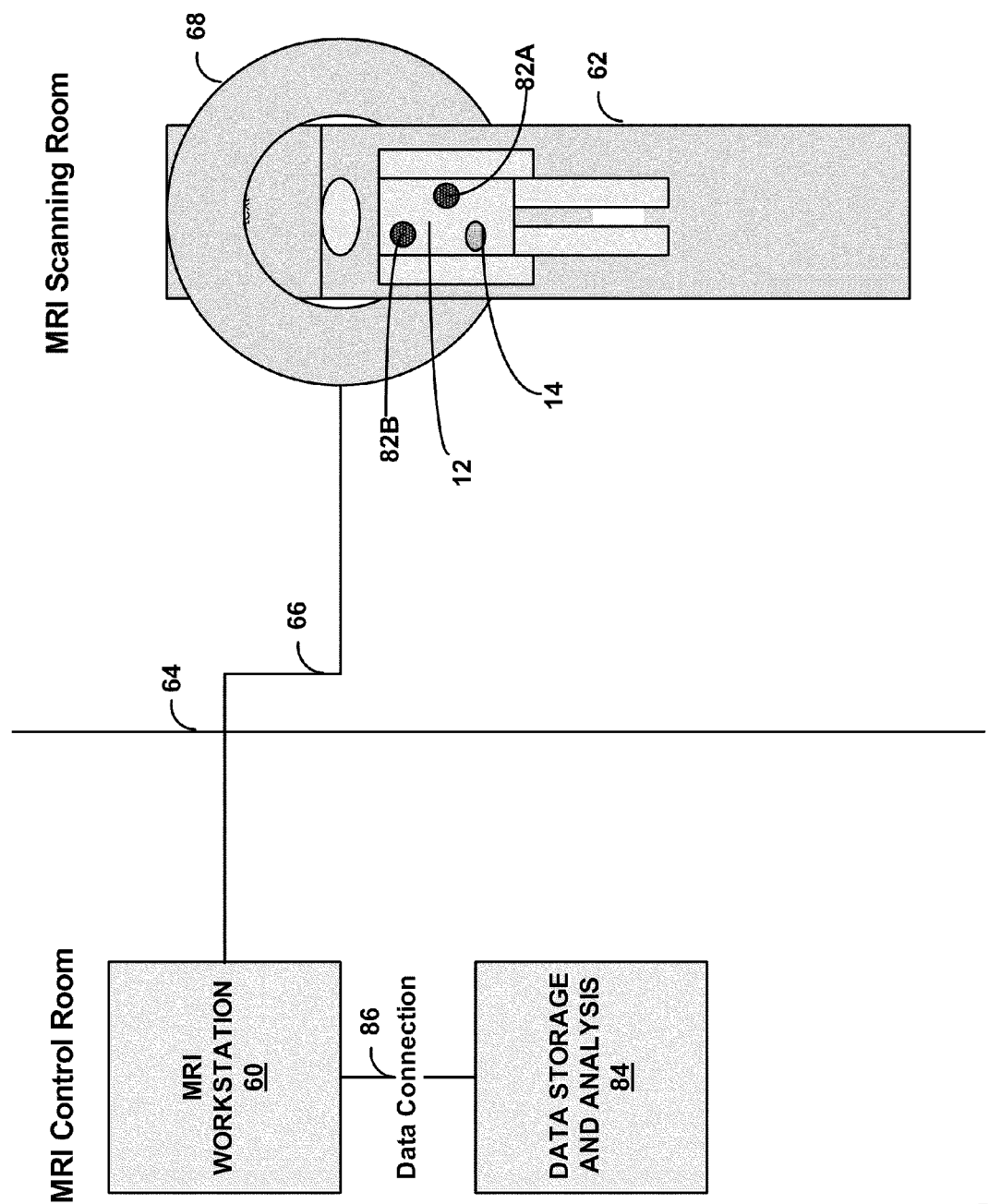
FIG. 9 is a block diagram illustrating another example system that may be used to coordinate changes in electrical stimulation therapy with an fMRI scan.

FIG. 9 is a block diagram illustrating another example system that may be used to coordinate changes in electrical stimulation therapy with an fMRI scan. FIG. 9 depicts external MRI-safe electrodes 82A, 82B (collectively "electrodes 82"), e.g., surface electromyography (EMG) electrodes, affixed externally to patient 12 in order to detect changes in stimulation therapy. For example, electrodes 82 may include relatively high impedance or optical circuitry or may be shielded in order to be MRI-safe. Electrodes 82 may also be a patch electrode, such as those used for trialing purposes.

Data received via electrodes 82 may be recorded by a device in communication with MRI workstation 60, e.g., data storage and analysis device 84. Data storage and analysis device 84 may analyze the data received and determine that therapy has changed, e.g., stimulation has stopped otherwise been altered. For example, a first set of patient data may be received and recorded to data storage and analysis device 84 prior to delivering electrical stimulation therapy to patient 12. Then, a second set of patient data may be received and recorded to data storage and analysis device 84 after electrical stimulation therapy is delivered to patient 12. The patient data may be, for example, one or more physiological parameters sensed by electrodes 82, where the parameters change as a function of electrical stimulation delivered by IMD 14. Example parameters include, but not limited to, muscle activity (e.g., sensed via EMG signals), body temperature (e.g., sensed via thermal sensing electrodes), cardiac activity (e.g., sensed via an ECG), brain activity (e.g., sensed via an EEG or ECoG), electrodermal activity, or respiratory activity. Thus, electrodes 82 can sense any suitable physiological parameter, such as, but not limited to, EMG signals, EEG signals, ECoG signals, ECG signals, or respiratory signals.

A processor in data storage and analysis device 84 may, for example, analyze the first and second sets of patient data and determine that therapy has changed, e.g., based on different physiological activity of patient 12 reflected by the first and second sets of patient data. As an example, if the first and second sets of patient data include respective EMG signals, the processor of data storage and analysis device 84 may compare a signal characteristic (e.g., a mean, median, peak or lowest amplitude, frequency, or a frequency domain characteristic) of the EMG signals to detect a change in the patient's response. A difference in the signal characteristic of the sensed EMG signals may indicate that electrical stimulation delivered by IMD 14 has changed, i.e., from one stimulation state to another, thereby resulting in the change in the patient data.

Upon determining that therapy has changed, data storage and analysis device 84 may communicate to MRI workstation 60, via data connection 86, that a change in electrical stimulation delivered by IMD 14 has occurred. In response, MRI workstation 60 may initiate an fMRI scan of patient 12. In some examples, data storage and analysis device 84 may determine the particular stimulation program being delivered by IMD 14, e.g., by interrogating IMD 14 and/or programmer 20, and communicate the program to MRI workstation 60. MRI workstation 60 can then associate the program with the fMRI scan taken while the stimulation according to the program was being delivered to patient 14.

In other examples, data connection 86 may be absent. In such an implementation, an operator may monitor data storage and analysis device 84 for an indication that therapy has changed. For example, data storage and analysis device 84 may include a display or speaker that notifies the operator that therapy is changing.

In some examples, IMD 14 is programmed prior to scanning of patient 12 by MRI unit 62 to change stimulation modes according to a predefined schedule. In other examples, such as depicted in FIG. 9, programmer 20 is configured to reprogram IMD 14, or otherwise change the electric stimulation delivered to patient 12 by IMD 14, according to predefined schedule. In order to reprogram IMD 14, programmer 20 is capable of distance communication with IMD 14. For example, telemetry circuit 40 of programmer 20 may be configured for distance telemetry. In addition, the system in FIG. 9 may further include an MRI safe telemetry extender (not shown) that extends from outside bore 68 to inside bore 68 of MRI unit 62 in order to allow programmer 20 to communicate with IMD 14.

Figure 10:
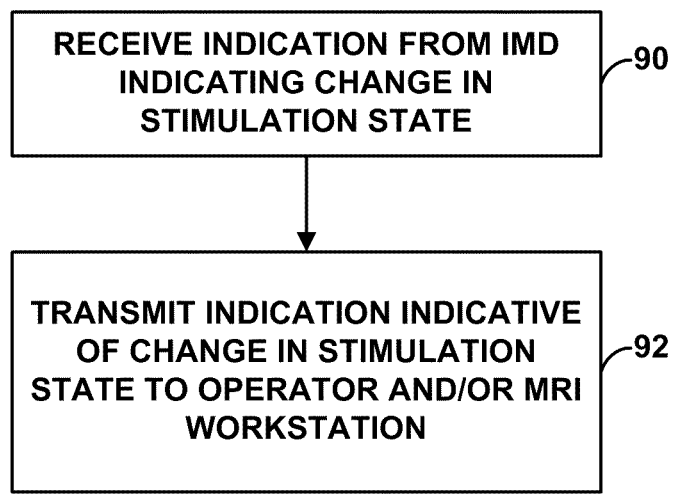
FIG. 10 is a flow diagram of an example technique that can be implemented to associate one or more fMRI scans with respective stimulation states without requiring the implantable medical device to be reprogrammed prior to each fMRI scan.

FIG. 10 is a flow diagram of an example technique that can be implemented to associate one or more fMRI scans with respective stimulation states (e.g., a specific therapy program or a state in which no electrical stimulation is delivered to patient 12) without requiring IMD 14 to be reprogrammed prior to each fMRI scan. Although the technique shown in FIG. 10 is described with respect to the system shown in FIG. 4, in other examples, the technique shown in FIG. 10 can be used with other systems comprising an MRI unit and an IMD.

The technique shown in FIG. 10 can be implemented while patient 12 is at least one of in MRI unit 62 or being imaged by MRI unit 61. In some examples, patient 12 is at least partially in bore 68 when being imaged by MRI unit 62. In FIG. 10, programmer 20 receives an indication from IMD 14 indicative of a change in a stimulation state (90). As discussed above, e.g., with respect to FIG. 4, the change in the stimulation state may be attributable to a cycling between multiple programs or between one or more programs and a state in which IMD 14 does not deliver any electrical stimulation is delivered to patient 12. In some examples, processor 34 (FIG. 3) of programmer 20 receives an indication from processor 24 (FIG. 2) of IMD 14 indicative of a change in a stimulation state when IMD 14 is in a cycling and scheduling mode in which IMD 14 automatically cycles between stimulation states in a predetermined schedule. Processor 24 may, for example, transmit a signal to programmer 20 via the respective telemetry circuits 28, 40 immediately prior to (e.g., 1 to 5 seconds) a change in a stimulation state. In other examples, programmer 20 is synched with IMD 14 such that IMD 14 does not need to transmit an indication of a change in stimulation state to programmer 20. Rather, processor 34 may determine when the next change in stimulation state is expected to occur based on the predetermined schedule and the synched clocks.

In other examples, programmer 20 receives an indication from IMD 14 indicative of a change in a stimulation state when processor 24 of IMD 14 selects a program for controlling stimulation generator 30 based on a detected patient state.

After programmer 20 receives an indication from IMD 14 indicative of a change in a stimulation state (90), processor 34 of programmer 20 can transmit an indication regarding the change in stimulation state to an operator of MRI workstation 60 or to MRI workstation 60 (92), either directly or indirectly via an intermediate device (e.g., controller device 72 shown in FIG. 6). In some examples, the operator can control MRI unit 62 to initiate an fMRI scan upon receiving the indication, while in other examples, MRI workstation 60 automatically (without user intervention) controls MRI unit 62 to initiate an fMRI scan upon receiving the indication. Initiating the fMRI scan based on the indication of a change in stimulation state helps the fMRI scan correspond in time to the stimulation state, such that the fMRI scan provides information relevant to assessing the stimulation state.

As discussed above, the fMRI scan may be correlated with the stimulation state in any one or more of a number of suitable ways for later analysis for the stimulation state (e.g., a specific program defining the stimulation state). For example, an operator may manually record the time when an fMRI scan was initiated and match up the time with a stimulation state that was known to be occurring at the same time (e.g., stored by IMD 14), the fMRI scans may be marked or annotated (e.g., via workstation 60) with data that identifies information related to the stimulation state (e.g., the stimulation program and/or stimulation parameters), and the like.

Figure 11:
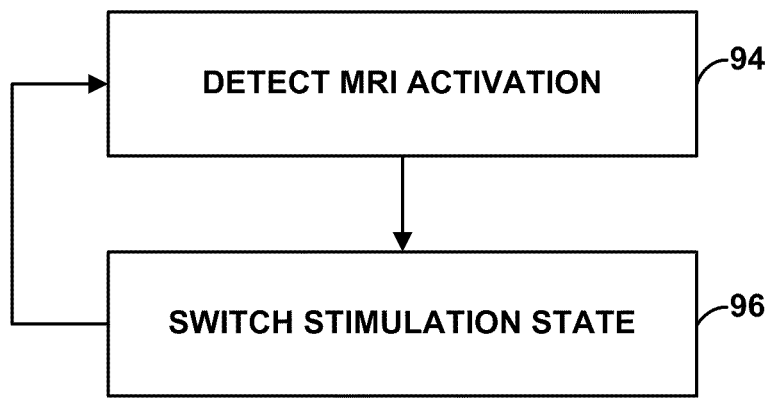
FIG. 11 is a flow diagram of another example technique that can be implemented to associate one or more fMRI scans with respective stimulation states of an implantable medical device without requiring the implantable medical device to be reprogrammed prior to each fMRI scan.

FIG. 11 is a flow diagram of another example technique that can be implemented to associate one or more fMRI scans with respective stimulation states of IMD 14 (e.g., a specific therapy program or a state in which no electrical stimulation is delivered to patient 12) without requiring IMD 14 to be reprogrammed prior to each fMRI scan. Although the technique shown in FIG. 10 is described with respect to the system shown in FIG. 4, in other examples, the technique shown in FIG. 10 can be used with other systems comprising an MRI unit and an IMD. FIG. 11 differs from the technique shown in FIG. 11 in that the fMRI scans may occur asynchronously, and, yet, still be associated with a stimulation state of IMD 14. This may provide the operator of MRI workstation 60 with more freedom in initiating the fMRI scans.

As with the technique shown in FIG. 10, the technique shown in FIG. 11 can be implemented while patient 12 is at least one of in MRI unit 62 or being imaged by MRI unit 61. In some examples, patient 12 is at least partially in bore 68 when being imaged by MRI unit 62. In the technique shown in FIG. 11, IMD 14 detects activation of MRI unit 62, which is indicative of the initiation of an fMRI scan (94). A sensor (e.g., a Hall effect sensor) configured to detect the MRI can be used to detect the MRI activation (94). For example, a sensor that is configured to detect the magnetic field generated by MRI unit 62 or a change in one or more properties of a magnetic field can be used to detect the initiation of an fMRI scan. The sensor can be incorporated as part of IMD 14 or may be separate from IMD 14 and in wired or wireless communication with IMD 14. The sensor can be configured to be MRI safe. Upon detecting MRI activation via the sensor (94), processor 24 (FIG. 2) of IMD 14 may switch stimulation states (96), such as by cycling to the prior stimulation state if IMD 14 cycles between two stimulation states or shifting to the next stimulation state (e.g., the next therapy program) in a sequence of stimulation states. In this way, the fMRI scan that was just initiated may be associated with a respective stimulation state of IMD 14.

In some examples, IMD 14 may maintain the stimulation state, e.g., by delivering stimulation according to the program associated with the state or by not delivering stimulation if the state is characterized by no electrical stimulation, until another, subsequent MRI activation is detected (94). The subsequent MRI activation may indicate, for example, the initiation of a second fMRI scan. Thereafter, processor 24 of IMD 14 may switch stimulation states (96), such that the second fMRI scan is associated with a different state. In other examples, IMD 14 may maintain the stimulation state, e.g., by delivering stimulation according to the program associated with the state or by not delivering stimulation if the state is characterized by no electrical stimulation, until MRI deactivation is detected via the sensor, and may not reinitiate another stimulation state until MRI activation is detected again (94).

Another aspect of the disclosure includes synchronizing the cycling of stimulation states by IMD 14 with MRI workstation 60 by transmitting from IMD 14 a specific stimulation pulse signal that may be detected by MRI unit 62. That is, in some examples, MRI unit 62 is configured to sense the particular stimulation program or regime that IMD 14 is delivering to patient 12. IMD 14 can transmit a non-therapeutic signal that indicates to MRI workstation 60, via MRI unit 62, that IMD 14 is beginning to deliver stimulation and, in some examples, the parameters of the stimulation program or some other information indicating the stimulation state (e.g., a specific program). In some examples, synchronization may be achieved via a special scanning sequence for MRI unit 62 that detects the non-therapeutic signals transmitted by IMD 14. Upon detecting a new stimulation state of IMD 14, e.g., based on the signal transmitted by IMD 14 and detected by MRI unit 62, MRI unit 62 may transmit an indication of the new stimulation state to MRI workstation 60 so that the stimulation state can be associated with the fMRI scan that coincides in time to the stimulation state.

As mentioned above, in some example configurations IMD 14 may be an external trial screening device rather than implantable device. In such a configuration, the leads may be at least partially externalized. The leads can be, for example, connected via MRI safe trialing cables to an external stimulator, or to a programmer in communication with an external stimulator, and the external stimulator is brought into MRI control room to allow the operator or other clinician to control the delivery of stimulation therapy to patient 12.

Another aspect of the disclosure that may be incorporated into one or more of the systems shown in FIGS. 4-9 allows patient 12 to indicate whether the therapy delivered by IMD 14 was effective. For instance, patient 12 may indicate via one or more buttons of programmer 20 that the therapy is effective. In other examples, patient 12 may provide a verbal indication, or if a camera exists within MRI unit 62, patient 12 may provide an indication using facial expressions. For patients with Parkinson's disease, other measurements of therapy effectiveness may be used. For example, one or more accelerometers may be used to detect and/or measure tremor in a patient's wrist. The patient's indication of therapy effectiveness may later be cross-correlated with the fMRI scans to determine effective electrical stimulation programs.

It should be noted that synchronization error might accumulate over the course of a scanning session. The accumulated error may be displayed to the operator via programmer 20, MRI workstation 60, controller device 72, indication device 80, and data storage and/or analysis device 84, for example. For example, programmer 20 in FIG. 4 may indicate that IMD 14 will begin delivering stimulation in 10 seconds +/−2 seconds. Thirty minutes later, programmer 20 may indicate that stimulation is cycling in 10 seconds +/−5 seconds. Then, one hour after the scanning session begins, programmer 20 may request that the operator resynchronize the programmer 20, for example, and IMD 14 due to the accumulated error.

Using the various techniques described above, fMRI scans may be coordinated with changes to electrical stimulation therapy programs, thereby providing a clinician with the ability to correlate scans and programs. Such coordination may reduce or eliminates the need to stop a scanning session, remove patient 14 from the bore of the MRI unit, and reprogram IMD 14.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

Various aspects of the disclosure have been described. These and other aspects are within the scope of the following claims.

The invention claimed is:

1. A method comprising:
    while a patient is in or being imaged by a magnetic resonance imaging (MRI) unit, generating an indication that indicates that a medical device that is configured to cycle electrical stimulation therapy between a plurality of stimulation states:
        (i) will cycle the electrical stimulation therapy according to a predetermined schedule, or
        (ii) has cycled the electrical stimulation therapy according to the predetermined schedule, or
        (iii) has cycled the electrical stimulation therapy, wherein, in (iii), the indication is based on a physiological parameter of the patient that changes as a function of the electrical stimulation therapy; and
    initiating an MRI scan of the patient via an MRI workstation based on the indication, wherein generating the indication comprises, prior to cycling the electrical stimulation therapy with the medical device, generating the indication that medical device will cycle electrical stimulation therapy.

2. The method of claim 1, wherein generating the indication comprises generating, via a computing device, at least one of a textual notification, a graphical notification, an audible notification or a somatosensory notification.

3. The method of claim 1, wherein generating the indication comprises generating an indication that indicates the medical device will at least one of:
    alternate between delivery of the electrical stimulation therapy according to a first program and no delivery of electrical stimulation therapy according to the predetermined schedule, or
    alternate delivery of the electrical stimulation therapy according to two or more programs according to the predetermined schedule.

4. The method of claim 1, wherein generating the indication comprises generating the indication with the medical device.

5. The method of claim 1, wherein generating the indication comprises:
   determining the predetermined schedule with which the medical device cycles between the plurality of stimulation states;
   determining the predetermined schedule indicates an imminent transition from a first stimulation state to a second stimulation state of the plurality of stimulation states; and
   generating the indication upon determining the predetermined schedule indicates the imminent transition from the first stimulation state to the second stimulation state of the plurality of stimulation states.

6. The method of claim 1, wherein generating the indication comprises generating the indication with a medical device programmer configured to communicate with the medical device.

7. The method of claim 6, wherein the MRI unit and the medical device are located in an MRI scanning room, the MRI workstation is located in an MRI control room, and the medical device programmer is located in the MRI control room when the MRI scan is initiated, wherein the medical device programmer is in communication with the MRI workstation, the method further comprising transmitting the indication from the medical device programmer to the MRI workstation.

8. The method of claim 6, wherein the MRI unit is located in an MRI scanning room, the MRI workstation is located in an MRI control room, and wherein the medical device programmer is located in the MRI control room when the MRI scan is initiated, wherein the medical device programmer is in communication with the MRI workstation, the method further comprising:
   transmitting the indication from the medical device programmer to the MRI workstation,
   wherein initiating the MRI scan of the patient via the MRI workstation comprises initiating, without manual intervention, the MRI scan of the patient via the MRI workstation in response to the transmission of the indication.

9. The method of claim 8, wherein the medical device programmer is in communication with the MRI workstation via an intermediary device, and wherein transmitting the indication from the programmer to the MRI workstation comprises transmitting the indication from the programmer to the MRI workstation via the intermediary device.

10. The method of claim 1, wherein initiating the MRI scan of the patient via the MRI workstation comprises initiating the MRI scan substantially simultaneously with the cycling of the electrical stimulation therapy with the medical device.

11. The method of claim 1, wherein the indication that the medical device will cycle the electrical stimulation therapy or has cycled the electrical stimulation therapy comprises an indication that the medical device will switch from a first stimulation state of the plurality of stimulation states to a second stimulation state of the plurality of stimulation states, the method further comprising associating the MRI scan with the second stimulation state.

12. A system comprising:
   an MRI workstation configured to control a magnetic resonance imaging (MRI) unit that is configured to generate an MRI scan of a patient;
   a medical device configured to deliver electrical stimulation therapy to the patient while the patient is in the MRI unit or being imaged by the MRI unit, wherein the medical device is configured to cycle electrical stimulation therapy between a plurality of stimulation states; and
   a processor configured to generate an indication that, while the patient is in the MRI unit or is being imaged by the MRI unit, the medical device:
      (i) will cycle the electrical stimulation therapy according to a predetermined schedule, or
      (ii) has cycled the electrical stimulation therapy according to the predetermined schedule, or
      (iii) has cycled the electrical stimulation therapy, wherein, in (iii) the indication is based on a physiological parameter of the patient that changes as a function of the electrical stimulation therapy,
   wherein the MRI workstation is configured to control the MRI unit to initiate the MM scan of the patient based upon the indication, and the processor is configured to generate the indication prior to cycling of the electrical stimulation therapy by the medical device.

13. The system of claim 12, wherein the indication comprises at least one of a textual notification, a graphical notification, an audible notification or a somatosensory notification.

14. The system of claim 12, wherein the medical device is configured to cycle between a plurality of stimulation states by at least one of alternating between delivery of the electrical stimulation therapy according to a first program and no delivery of electrical stimulation therapy, or alternating between delivery of the electrical stimulation therapy according to the first program and delivery of the electrical stimulation therapy according to a second program.

15. The system of claim 12, wherein the medical device comprises the processor.

16. The system of claim 12, wherein the processor is configured to determine the predetermined schedule with which the medical device cycles between the plurality of stimulation states, and generate the indication upon determining the predetermined schedule indicates the imminent transition from a first stimulation state to a second stimulation state of the plurality of stimulation states.

17. The system of claim 12, further comprising a medical device programmer configured to communicate with the medical device, wherein the medical device programmer comprises the processor.

18. The system of claim 17, wherein the MRI unit is located in an MRI scanning room, the MRI workstation is located in an MRI control room, the medical device programmer is located in the MRI control room when the MRI scan is initiated.

19. The system of claim 17, wherein the medical device programmer is configured to communicate with the MRI workstation, and wherein the device programmer is configured to transmit the indication to the MRI workstation, and the MRI workstation is configured to initiate the MRI scan without manual intervention in response to the transmission of the indication.

20. The system of claim 17, further comprising an intermediary device, wherein the medical device programmer is configured to transmit the indication to the MRI workstation via the intermediary device, which is configured to communicate with the medical device programmer and the Mill workstation.

21. The system of claim 12, wherein the MRI unit is located in an MRI scanning room, the MRI workstation is located in an MRI control room, and a medical device programmer is located in the MRI scanning room when the MRI scan is initiated, wherein the programmer is configured to, in response to a first signal from the MRI workstation, transmit a second signal to the medical device that controls the cycling of the medical device.

22. The system of claim 12, wherein the medical device is configured to cycle the electrical stimulation therapy substantially simultaneously with the MRI scan of the patient by the MRI workstation.

23. A method comprising:
while a patient is in or being imaged by a magnetic resonance imaging (MRI) unit, generating an indication that indicates that a medical device that is configured to cycle electrical stimulation therapy between a plurality of stimulation states:
(i) will cycle the electrical stimulation therapy according to a predetermined schedule, or
(ii) has cycled the electrical stimulation therapy according to the predetermined schedule, or
(iii) has cycled the electrical stimulation therapy, wherein, in (iii), the indication is based on a physiological parameter of the patient that changes as a function of the electrical stimulation therapy, wherein the indication comprises a first indication;
receiving a second indication that the electrical stimulation therapy was efficacious; and
initiating an MRI scan of the patient via an MRI workstation after generating the first indication and after receiving the second indication that the electrical stimulation therapy was efficacious.

24. A method comprising:
sensing a physiological parameter of a patient that changes as a function of electrical stimulation therapy delivered to the patient;
determining a medical device configured to cycle the electrical stimulation therapy between a plurality of stimulation states has cycled the electrical stimulation therapy based on the sensed physiological parameter; and
while the patient is in or being imaged by a magnetic resonance imaging (MRI) unit, generating an indication that indicates that the medical device has cycled the electrical stimulation therapy after determining the medical device has cycled the electrical stimulation therapy based on the sensed physiological parameter; and
initiating an MRI scan of the patient via an MRI workstation based on the indication.

25. A system comprising:
an MRI workstation configured to control a magnetic resonance imaging (MRI) unit that is configured to generate an MRI scan of a patient;
a medical device configured to deliver electrical stimulation therapy to the patient while the patient is in the MRI unit or being imaged by the MRI unit, wherein the medical device is configured to cycle electrical stimulation therapy between a plurality of stimulation states; and
a processor configured to generate an indication that, while the patient is in the MRI unit or is being imaged by the MRI unit, the medical device:
(i) will cycle the electrical stimulation therapy according to a predetermined schedule, or
(ii) has cycled the electrical stimulation therapy according to the predetermined schedule, or
(iii) has cycled the electrical stimulation therapy, wherein, in (iii) the indication is based on a physiological parameter of the patient that changes as a function of the electrical stimulation therapy,
wherein the indication comprises a first indication, and the processor is configured to receive a second indication that the electrical stimulation therapy was efficacious, wherein the MRI workstation is configured to control the MRI unit to initiate the MRI scan of the patient after the processor generates the first indication and after the processor receives the second indication that the electrical stimulation therapy was efficacious.

26. A system comprising:
an MRI workstation configured to control a magnetic resonance imaging (MRI) unit that is configured to generate an MRI scan of a patient;
a medical device configured to deliver electrical stimulation therapy to the patient while the patient is in the MRI unit or being imaged by the MRI unit, wherein the medical device is configured to cycle electrical stimulation therapy between a plurality of stimulation states; and
a processor configured to generate an indication that, while the patient is in the MRI unit or is being imaged by the MRI unit, the medical device:
(i) will cycle the electrical stimulation therapy according to a predetermined schedule, or
(ii) has cycled the electrical stimulation therapy according to the predetermined schedule, or
(iii) has cycled the electrical stimulation therapy, wherein, in (iii) the indication is based on a physiological parameter of the patient that changes as a function of the electrical stimulation therapy,
wherein the indication comprises an indication that the medical device will switch from a first stimulation state to a second stimulation state, wherein the Mill workstation is configured to associate the Mill scan with the second stimulation state, and wherein the MRI workstation is configured to control the MRI unit to initiate the MRI scan of the patient based upon the indication.

27. A system comprising:
an MRI workstation configured to control a magnetic resonance imaging (MRI) unit that is configured to generate an MRI scan of a patient;
a medical device configured to deliver electrical stimulation therapy to the patient while the patient is in the MRI unit or being imaged by the MRI unit, wherein the medical device is configured to cycle electrical stimulation therapy between a plurality of stimulation states; and
a processor configured to generate an indication that, while the patient is in the MRI unit or is being imaged by the MRI unit, the medical device:
(i) will cycle the electrical stimulation therapy according to a predetermined schedule, or
(ii) has cycled the electrical stimulation therapy according to the predetermined schedule, or
(iii) has cycled the electrical stimulation therapy, wherein, in (iii) the indication is based on a physiological parameter of the patient that changes as a function of the electrical stimulation therapy; and
a sensor configured to sense the physiological parameter of the patient that changes as a function of the electrical stimulation therapy,
wherein the MRI workstation is configured to control the MRI unit to initiate the MRI scan of the patient based upon the indication, and the processor is configured to determine the medical device has cycled electrical stimulation therapy based on the sensed physiological parameter and generate the indication that that the medical device has cycled electrical stimulation therapy after determining the medical device has cycled electrical stimulation therapy based on the sensed physiological parameter.

28. A system comprising:

means for delivering electrical stimulation therapy to a patient in a magnetic resonance imaging (MRI) unit according to a first program of a plurality of programs stored in a medical device, wherein the means for delivering electrical stimulation therapy is configured to cycle electrical stimulation therapy between a plurality of stimulation states, the first program being associated with a first stimulation state of the plurality of stimulation states;

means for generating an indication that, while the patient is in the MRI unit or is being imaged by the MRI unit, the medical device:
  (i) will cycle the electrical stimulation therapy according to a predetermined schedule, or
  (ii) has cycled the electrical stimulation therapy according to the predetermined schedule, or
  (iii) has cycled the electrical stimulation therapy, wherein, in (iii) the indication is based on a physiological parameter of the patient that changes as a function of the electrical stimulation therapy; and means for initiating an MRI scan of the patient via an MRI workstation based on the indication, wherein the means for generating the indication is configured to generate the indication prior to cycling of the electrical stimulation therapy by the means for delivering electrical stimulation therapy.

29. The system of claim 28, further comprising means for associating the MRI scan with one stimulation state of the plurality of stimulation states.

30. A method comprising:

receiving an indication that a medical device delivering electrical stimulation therapy to a patient in a magnetic resonance imaging (MRI) unit will switch from a first stimulation state to a second stimulation state prior to the medical device switching from the first stimulation state to the second stimulation state, wherein the medical device switches stimulation states without intervention from a user;

while the medical device is in the second stimulation state, generating an Mill scan of the patient via an MRI unit based on the indication; and associating the second stimulation state with the MRI scan.

31. The method of claim 30, wherein receiving the indication comprises receiving the indication at an MRI workstation from at least one of the medical device or a medical device programmer configured to communicate with the medical device.

32. The method of claim 30, wherein the indication that the medical device will switch from the first stimulation state to the second stimulation state comprises an indication that the medical device will switch from delivery of electrical stimulation therapy according to a first program to a state in which all electrical stimulation is stopped, or will switch from delivery of electrical stimulation therapy according to the first program to delivery of the electrical stimulation therapy according to a second program.

33. A system comprising:

a magnetic resonance imaging (MRI) unit configured to generate an Mill scan of a patient;

a medical device configured to deliver electrical stimulation therapy to the patient while the patient is in the MRI unit or being imaged by the MRI unit, wherein the medical device is configured to switch between a plurality of different stimulation states without intervention from a user; and a processor configured to receive an indication that the medical device will switch from a first stimulation state to a second stimulation state prior to the medical device switching from the first stimulation state to the second stimulation state, and, while the medical device is in the second stimulation state, control the MRI unit to generate an MRI scan of the patient via an MM unit based on the indication and associate the second stimulation state with the MRI scan.

34. The system of claim 33, further comprising an MRI workstation that comprises the processor, wherein the processor is configured to receive the indication from at least one of the medical device or a medical device programmer configured to communicate with the medical device.

35. The system of claim 33, wherein the indication that the medical device will switch from the first stimulation state to the second stimulation state comprises an indication that the medical device will switch from delivery of electrical stimulation therapy according to a first program to a state in which all electrical stimulation is stopped, or will switch from delivery of electrical stimulation therapy according to the first program to delivery of the electrical stimulation therapy according to a second program.

36. A system comprising:

means for receiving an indication that a medical device delivering electrical stimulation therapy to a patient in a magnetic resonance imaging (MRI) unit will switch from a first stimulation state to a second stimulation state prior to the medical device switching from the first stimulation state to the second stimulation state, wherein the medical device switches stimulation states without intervention from a user;

means for generating an MRI scan of the patient via an MRI unit based on the indication while the medical device is in the second stimulation state; and means for associating the second stimulation state with the MRI scan.

* * * * *